United States Patent
Allwein et al.

(10) Patent No.: US 9,115,147 B2
(45) Date of Patent: Aug. 25, 2015

(54) TRICYCLIC DERIVATIVES AND THEIR PHARMACEUTICAL USE AND COMPOSITIONS

(75) Inventors: Shawn P. Allwein, Downingtown, PA (US); George C. Morton, Collegeville, PA (US); Gerard C. Rosse, Poway, CA (US); Yi Wang, Chester Springs, PA (US)

(73) Assignee: Cephalon, Inc., Frazer, PA (US)

( * ) Notice: Subject to any disclaimer, the term of this patent is extended or adjusted under 35 U.S.C. 154(b) by 220 days.

(21) Appl. No.: 13/529,369

(22) Filed: Jun. 21, 2012

(65) Prior Publication Data

US 2012/0277186 A1 Nov. 1, 2012

Related U.S. Application Data

(63) Continuation of application No. PCT/US2010/060938, filed on Dec. 17, 2010.

(60) Provisional application No. 61/289,095, filed on Dec. 22, 2009.

(51) Int. Cl.
*A61K 31/695* (2006.01)
*C07D 491/052* (2006.01)

(52) U.S. Cl.
CPC ................... *C07D 491/052* (2013.01)

(58) Field of Classification Search
None
See application file for complete search history.

(56) References Cited

PUBLICATIONS

Anderson (Chem and Biol 10:787-797, 2003).*
Thiel (Nature Biotechnol 2:513-519, 2004).*

* cited by examiner

*Primary Examiner* — Craig Ricci

(57) ABSTRACT

This application relates to tricyclic compounds of Formula I:

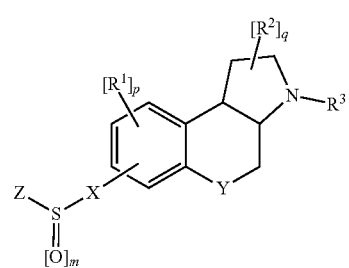

including all stereoisomeric forms, all mixtures of stereoisomeric forms, and salts of these compounds. This application also relates to compositions comprising compounds of Formula I, stereoisomeric forms, all mixtures of stereoisomeric forms, and salts thereof and uses therefor.

7 Claims, No Drawings

TRICYCLIC DERIVATIVES AND THEIR PHARMACEUTICAL USE AND COMPOSITIONS

CROSS-REFERENCE TO RELATED APPLICATIONS

This application is a continuation of International Application No. PCT/US2010/060938, filed Dec. 17, 2010, which claims priority to U.S. Provisional Application Ser. No. 61/289,095, filed Dec. 22, 2009. The disclosures of the aforementioned applications are incorporated herein by reference in their entireties for all purposes.

SUMMARY

This application relates to tricyclic compounds of Formula I:

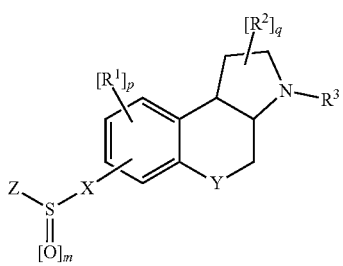

including all stereoisomeric forms and all mixtures of stereoisomeric forms of these compounds.

This application also relates to salts of the compounds of Formula I and compositions comprising compounds of Formula I or salts of compounds of Formula I.

This application further relates to pharmaceutically acceptable salts of the compounds of Formula I and pharmaceutical compositions comprising compounds of Formula I or pharmaceutically acceptable salts of the compounds of Formula I.

The compounds of Formula I and/or their pharmaceutically acceptable salts are useful for treating conditions, disorders and diseases that are directed or indirectly controlled, mediated, effected or influenced by one or more members of the serotonin receptor (5-HT) family, such as for example, the 5-HT$_6$ and 5-HT$_7$ receptors.

Compounds of Formula I are 5-HT$_6$ receptor ligands and are therefore useful in the treatment of various conditions, disorders or diseases such as those related to the central nervous system (CNS) and the gastrointestinal (GI) tract.

It should be understood that the section titles used in this application are for indexing and search purposes only and should not be construed as limiting in any way.

BACKGROUND

Serotonin has been implicated in a number of conditions, disorders and diseases that originate in the central nervous system. These include conditions, disorders and diseases related to mood, cognitive function, sleeping, eating, pain, depression, anxiety, schizophrenia, and other bodily states. Serotonin also plays an important role in peripheral systems, such as the gastrointestinal system where it has been found to mediate a variety of contractile, secretory, and electrophysiologic effects.

The superfamily of serotonin receptors (5-HT) includes 7 classes (5-HT$_1$-5-HT$_7$) encompassing 14 human subclasses which modulate the effects of the neurotransmitter 5-hydroxytryptamine (5-HT, serotonin). The 5-HT$_6$ receptor is the latest serotonin receptor to be identified by molecular cloning both in rats and in humans. *Mol. Pharmacol*, 1993, 43, 320-327; *J Neurochem*, 1996, 66, 47-56. The human 5-HT$_6$ receptor is a 440 amino acid polypeptide with seven transmembrane spanning domains which is consistent with the structure of a G protein-coupled receptor (GPCR). There is about 89% sequence homology between 5-HT$_6$ receptors in human and rat and the relative distribution of 5-HT$_6$ receptor mRNA in the brain also appears to be similar. Together, these observations suggest that the rat is an appropriate model for predicting the pharmacology of 5-HT$_6$ receptor ligands in humans.

The 5-HT$_6$ receptor is primarily present in the central nervous system and is involved in glutamatergic and cholinergic neuronal activity. *Curr Drug Targets CNS Neurol Disord*, 2004, 3, 59-79. Blocking the function of 5-HT$_6$ receptors has been found to increase acetylcholine (ACh) and glutamate-mediated neurotransmission, and enhance cognitive processes. Several antidepressants and atypical antipsychotics have also been shown to bind to the 5-HT$_6$ receptor with high affinity. This binding may be a contributing factor in the therapeutic profile of these drugs. 5-HT$_6$ receptor activity has also been linked to generalized states of stress and anxiety. *Life Sciences*, 1998, 62, 1473-1477. Taken together, these studies and observations suggest that compounds with 5-HT$_6$ receptor affinity may be useful for the treatment of various conditions, disorders or diseases related to the central nervous system (CNS) such as cognitive diseases, neurodegenerative diseases, schizophrenia, anxiety, and depression. Other CNS-related conditions, disorders or diseases that may be affected by modulating 5-HT$_6$ receptor activity include sleep/wakefulness disorders as well as nociception, i.e., the neural processes of encoding and processing noxious stimuli.

The 5-HT$_6$ receptor has also been shown to play a role in conditions, disorders or diseases that relate to food ingestion or food intake, such as, for example, anorexia, cachexia, and obesity. See, for example, *Drug Discovery Today*, 2006, 11, 283-299. The 5-HT$_6$ receptor is also thought to be involved in conditions, disorders or diseases related to the gastrointestinal (GI) tract, such as irritable bowel syndrome and functional bowel disorder.

Given the broad spectrum of physiologic effects that are mediated by serotonin there is a tremendous amount of interest in identifying and developing compounds that affect serotonergic systems, including those conditions, disorders or diseases that are directly or indirectly mediated, controlled, effected or influenced by the 5-HT$_6$ receptor. Compounds that have an affinity for, interact with, stimulate, or inhibit the 5-HT$_6$ receptor are commonly referred to as 5-HT$_6$ ligands.

This application relates to new compounds with affinity for the 5-HT$_6$ receptor, i.e., 5-HT$_6$ ligands, which may be useful as active ingredients in pharmaceutical preparations for the treatment of certain conditions, disorders or diseases related to the central nervous system (CNS) such as memory disorders, anxiety, epilepsy, migraine, panic attacks, depression, bipolar disorder, obsessive compulsive disorders, cognition/cognitive disorders, mild cognitive impairment (MCI), senile dementia, psychosis, schizophrenia, ADHD/ADD; or for the treatment of pain including neuropathic pain and chronic pain; head trauma or injury; or for the treatment of neurodegenerative conditions, disorders or diseases such as Alzheimer's disease, Parkinson's disease, Huntington's disease, amyotrophic lateral sclerosis (ALS) or multiple sclerosis; or for the treatment of conditions, disorders or diseases related to addiction and/or withdrawal from substances such as narcotics, ethanol (alcoholism), nicotine, and/or benzodiazepines; sleep/wakefulness disorders; or for the treatment of gastrointestinal (GI) conditions, disorders or diseases such as irritable bowel syndrome (IBS), functional bowel disorder; or for the treatment of conditions, disorders or diseases related to feeding behaviors or food intake such as anorexia, cachexia, and obesity.

These compounds may also be useful for the improvement of cognition (cognitive enhancement) and/or improvement of memory in otherwise healthy subjects.

DETAILED DESCRIPTION

The following provides additional non-limiting details of the compounds of Formula I, compounds of Formulae II through V, as well as various species and more specific embodiments of the same, intermediates, and other compounds of interest.

As used herein, the term "compound(s) of Formula I" should be understood as including compounds of Formulae II through V, unless expressly stated to the contrary.

As used herein, the term "compound(s)" whether used by itself or in combination with any Formula should be understood as including all stereoisomers, all mixtures of stereoisomers, and all salts of such compounds, stereoisomers, and mixtures of stereoisomers, unless expressly stated to the contrary. Accordingly, use of the phrase "compound(s) of Formula I or salts thereof" refers to and includes compounds of Formulae I through Formula V, all stereoisomers, all mixtures of stereoisomers, and all salts of such compounds, stereoisomers, and mixtures of stereoisomers. This understanding extends to pharmaceutical compositions and methods of treatment that employ or comprise one or more compounds of Formula I.

One aspect of this application is directed to compounds of Formula I:

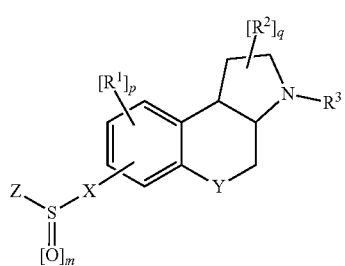

or salts thereof wherein:

$R^1$ at each occurrence is independently selected from H, halogen, CN, $NO_2$, $NR^5R^6$, $COR^5$, $CO_2R^5$, $CONR^5$, $NCOR^5$, $(C_1-C_6)$alkyl, $(C_1-C_6)$alkoxy, $(C_1-C_6)$haloalkyl, $(C_1-C_6)$alkyl$(C_1-C_6)$alkoxy, $(C_1-C_6)$alkyl$(C_1-C_6)$haloalkoxy, $(C_3-C_{10})$cycloalkyl, $(C_1-C_6)$alkyl$(C_3-C_{10})$cycloalkyl, $(C_6-C_{10})$aryl, $(C_6-C_{10})$aryloxy, $(C_1-C_6)$alkoxy$(C_6-C_{10})$aryl, $(C_1-C_6)$alkyl$(C_6-C_{10})$aryl, $(C_2-C_9)$heterocycloalkyl, $(C_2-C_9)$heterocycloalkyloxy, $(C_1-C_6)$alkoxy$(C_2-C_9)$heterocycloalkyl, $(C_1-C_6)$alkyl$(C_2-C_9)$heterocycloalkyl, $(C_5-C_9)$heteroaryl, $(C_5-C_9)$heteroaryloxy, $(C_1-C_6)$alkoxy$(C_5-C_9)$heteroaryl, and $(C_1-C_6)$alkyl$(C_5-C_9)$heteroaryl, and p is 0, 1, 2 or 3, wherein any of the foregoing, except for H, halogen, CN, and $NO_2$, is optionally substituted with one or more substituents;

$R^2$ at each occurrence is independently selected from H, $(C_1-C_6)$alkyl, $(C_6-C_{10})$aryl, and $(C_1-C_6)$alkyl$(C_6-C_{10})$aryl and q is 0, 1, or 2;

$R^3$ is selected from H, $(C_1-C_6)$alkyl, $(C_1-C_6)$hydroxyalkyl, $(C_1-C_6)$haloalkyl, $(C_1-C_6)$alkyl$(C_1-C_6)$alkoxy, $CO(C_1-C_6)$alkyl, $CONH(C_1-C_6)$alkyl, $CO_2(C_1-C_6)$alkyl, $SO_2(C_1-C_6)$alkyl, $SO_2NH(C_1-C_6)$alkyl, $CO(C_6-C_{10})$aryl, $CONH(C_6-C_{10})$aryl, $CO_2(C_6-C_{10})$aryl, $SO_2(C_6-C_{10})$aryl, $SO_2NH(C_6-C_{10})$aryl, $(C_6-C_{10})$aryl, $(C_1-C_6)$alkyl$(C_6-C_{10})$aryl, $(C_3-C_{10})$cycloalkyl, $CO(C_3-C_{10})$cycloalkyl, $CONH(C_3-C_{10})$cycloalkyl, $CO_2(C_3-C_{10})$cycloalkyl, $SO_2(C_3-C_{10})$cycloalkyl, $SO_2NH(C_3-C_{10})$cycloalkyl, $(C_1-C_6)$alkyl$(C_3-C_{10})$cycloalkyl, $CO(C_1-C_6)$alkyl$(C_3-C_{10})$cycloalkyl, $CONH(C_1-C_6)$alkyl$(C_3-C_{10})$cycloalkyl, $CO_2(C_1-C_6)$alkyl$(C_3-C_{10})$cycloalkyl, $SO_2(C_1-C_6)$alkyl$(C_3-C_{10})$cycloalkyl, $SO_2NH(C_1-C_6)$alkyl$(C_3-C_{10})$cycloalkyl, $(C_2-C_9)$heterocycloalkyl, $(C_1-C_6)$alkyl$(C_2-C_9)$heterocycloalkyl, $CONH(C_1-C_6)$alkyl$(C_2-C_9)$heterocycloalkyl, $CO(C_1-C_6)$alkyl$(C_2-C_9)$heterocycloalkyl, $CO_2(C_1-C_6)$alkyl$(C_2-C_9)$heterocycloalkyl, $SO_2(C_1-C_6)$alkyl$(C_2-C_9)$heterocycloalkyl, $SO_2NH(C_1-C_6)$alkyl$(C_2-C_9)$heterocycloalkyl, $(C_5-C_9)$heteroaryl, $CO(C_5-C_9)$heteroaryl, $CONH(C_5-C_9)$heteroaryl, $CO_2(C_5-C_9)$heteroaryl, $SO_2(C_5-C_9)$heteroaryl, $SO_2NH(C_5-C_9)$heteroaryl, $(C_1-C_6)$alkyl$(C_5-C_9)$heteroaryl, $CO(C_1-C_6)$alkyl$(C_5-C_9)$heteroaryl, $CONH(C_1-C_6)$alkyl$(C_5-C_9)$heteroaryl, $SO_2(C_1-C_6)$alkyl$(C_5-C_9)$heteroaryl, $SO_2NH(C_1-C_6)$alkyl$(C_5-C_9)$heteroaryl, and $CO_2(C_1-C_6)$alkyl$(C_5-C_9)$heteroaryl, wherein any of the foregoing, except for H, is optionally substituted with one or more substituents and provided that $(C_5-C_9)$heteroaryl is not optionally substituted 1,3,4 triazole in any of $(C_1-C_6)$alkyl$(C_5-C_9)$heteroaryl, $CO(C_1-C_6)$alkyl$(C_5-C_9)$heteroaryl, $CONH(C_1-C_6)$alkyl$(C_5-C_9)$heteroaryl, and $CO_2(C_1-C_6)$alkyl$(C_5-C_9)$heteroaryl;

Y is $CH_2$ or O;

X is absent, O, $NR^4$, or $(C_1-C_4)$alkyl;

$R^4$ is H or $(C_1-C_6)$alkyl;

$R^5$ and $R^6$ at every occurrence are each independently selected from H, $(C_1-C_6)$alkyl, $(C_1-C_6)$haloalkyl, $(C_6-C_{10})$aryl, $(C_1-C_6)$alkyl$(C_6-C_{10})$aryl, $(C_2-C_9)$heterocycloalkyl, $(C_1-C_6)$alkyl$(C_2-C_9)$heterocycloalkyl, $(C_5-C_9)$heteroaryl, and $(C_1-C_6)$alkyl$(C_5-C_9)$heteroaryl, wherein any of the foregoing, except for H, is optionally substituted with one or more substituents;

m is 1 or 2; and

Z is selected from $(C_3-C_{10})$cycloalkyl, $(C_1-C_6)$alkyl$(C_3-C_{10})$cycloalkyl, $(C_2-C_9)$heterocycloalkyl, $(C_1-C_6)$alkyl$(C_2-C_9)$heterocycloalkyl, $(C_6-C_{10})$aryl, $(C_1-C_6)$alkyl$(C_6-C_{10})$aryl, $(C_5-C_9)$heteroaryl, and $(C_1-C_6)$alkyl$(C_5-C_9)$heteroaryl wherein any of the foregoing is optionally substituted with one or more substituents; or Z is $NR^8R^9$ wherein $R^8$ and $R^9$ are each independently selected from H, $(C_1-C_6)$alkyl, $(C_3-C_{10})$cycloalkyl, $(C_1-C_6)$alkyl$(C_3-C_{10})$cycloalkyl, $(C_6-C_{10})$aryl, $(C_1-C_6)$alkyl$(C_6-C_{10})$aryl, $(C_2-C_9)$heterocycloalkyl, $(C_1-C_6)$alkyl$(C_2-C_9)$heterocycloalkyl, $(C_5-C_9)$heteroaryl, and $(C_1-C_6)$alkyl$(C_5-C_9)$heteroaryl, wherein any of the foregoing, with the exception of H is optionally substituted with one or more substituents and provided that $R^8$ and $R^9$ are not both H; or $R^8$ and $R^9$ are taken together to form a $(C_2-C_9)$heterocycloalkyl ring that is optionally substituted with one or more substituents.

Another aspect of this application is directed to compounds of Formula II:

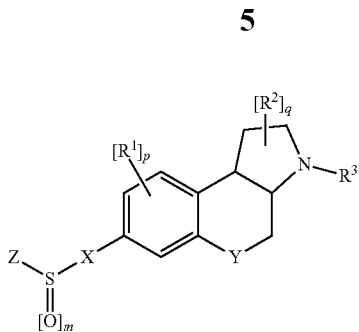

or a salt thereof, wherein:

$R^1$ at each occurrence is independently selected from H, halogen, CN, $NO_2$, $NR^5R^6$, $COR^5$, $CO_2R^5$, $CONR^5$, $NCOR^5$, $(C_1-C_6)$alkyl, $(C_1-C_6)$alkoxy, $(C_1-C_6)$haloalkyl, $(C_1-C_6)$alkyl$(C_1-C_6)$alkoxy, $(C_1-C_6)$alkyl$(C_1-C_6)$haloalkoxy, $(C_3-C_{10})$cycloalkyl, $(C_1-C_6)$alkyl$(C_3-C_{10})$cycloalkyl, $(C_6-C_{10})$aryl, $(C_6-C_{10})$aryloxy, $(C_1-C_6)$alkoxy$(C_6-C_{10})$aryl, $(C_1-C_6)$alkyl$(C_6-C_{10})$aryl, $(C_2-C_9)$heterocycloalkyl, $(C_2-C_9)$heterocycloalkyloxy, $(C_1-C_6)$alkoxy$(C_2-C_9)$heterocycloalkyl, $(C_1-C_6)$alkyl$(C_2-C_9)$heterocycloalkyl, $(C_5-C_9)$heteroaryl, $(C_5-C_9)$heteroaryloxy, $(C_1-C_6)$alkoxy$(C_5-C_9)$heteroaryl, and $(C_1-C_6)$alkyl$(C_5-C_9)$heteroaryl, and p is 0, 1, 2 or 3, wherein any of the foregoing, except for H, halogen, CN, and $NO_2$, is optionally substituted with one or more substituents;

$R^2$ at each occurrence is independently selected from H, $(C_1-C_6)$alkyl, $(C_6-C_{10})$aryl, and $(C_1-C_6)$alkyl$(C_6-C_{10})$aryl and q is 0, 1, or 2;

$R^3$ is selected from H, $(C_1-C_6)$alkyl, $(C_1-C_6)$hydroxyalkyl, $(C_1-C_6)$haloalkyl, $(C_1-C_6)$alkyl$(C_1-C_6)$alkoxy, $CO(C_1-C_6)$alkyl, $CONH(C_1-C_6)$alkyl, $CO_2(C_1-C_6)$alkyl, $SO_2(C_1-C_6)$alkyl, $SO_2NH(C_1-C_6)$alkyl, $CO(C_6-C_{10})$aryl, $CONH(C_6-C_{10})$aryl, $CO_2(C_6-C_{10})$aryl, $SO_2(C_6-C_{10})$aryl, $SO_2NH(C_6-C_{10})$aryl, $(C_6-C_{10})$aryl, $(C_1-C_6)$alkyl$(C_6-C_{10})$aryl, $(C_3-C_{10})$cycloalkyl, $CO(C_3-C_{10})$cycloalkyl, $CONH(C_3-C_{10})$cycloalkyl, $CO_2(C_3-C_{10})$cycloalkyl, $SO_2(C_3-C_{10})$cycloalkyl, $SO_2NH(C_3-C_{10})$cycloalkyl, $(C_1-C_6)$alkyl$(C_3-C_{10})$cycloalkyl, $CO(C_1-C_6)$alkyl$(C_3-C_{10})$cycloalkyl, $CONH(C_1-C_6)$alkyl$(C_3-C_{10})$cycloalkyl, $CO_2(C_1-C_6)$alkyl$(C_3-C_{10})$cycloalkyl, $SO_2(C_1-C_6)$alkyl$(C_3-C_{10})$cycloalkyl, $SO_2NH(C_1-C_6)$alkyl$(C_3-C_{10})$cycloalkyl, $(C_2-C_9)$heterocycloalkyl, $(C_1-C_6)$alkyl$(C_2-C_9)$heterocycloalkyl, $CONH(C_1-C_6)$alkyl$(C_2-C_9)$heterocycloalkyl, $CO(C_1-C_6)$alkyl$(C_2-C_9)$heterocycloalkyl, $CO_2(C_1-C_6)$alkyl$(C_2-C_9)$heterocycloalkyl, $SO_2(C_1-C_6)$alkyl$(C_2-C_9)$heterocycloalkyl, $SO_2NH(C_1-C_6)$alkyl$(C_2-C_9)$heterocycloalkyl, $(C_5-C_9)$heteroaryl, $CO(C_5-C_9)$heteroaryl, $CONH(C_5-C_9)$heteroaryl, $CO_2(C_5-C_9)$heteroaryl, $SO_2(C_5-C_9)$heteroaryl, $SO_2NH(C_5-C_9)$heteroaryl, $(C_1-C_6)$alkyl$(C_5-C_9)$heteroaryl, $CO(C_1-C_6)$alkyl$(C_5-C_9)$heteroaryl, $CONH(C_1-C_6)$alkyl$(C_5-C_9)$heteroaryl, $SO_2(C_1-C_6)$alkyl$(C_5-C_9)$heteroaryl, $SO_2NH(C_1-C_6)$alkyl$(C_5-C_9)$heteroaryl, and $CO_2(C_1-C_6)$alkyl$(C_5-C_9)$heteroaryl, wherein any of the foregoing, except for H, is optionally substituted with one or more substituents and provided that $(C_5-C_9)$heteroaryl is not optionally substituted 1,3,4 triazole in any of $(C_1-C_6)$alkyl$(C_5-C_9)$heteroaryl, $CO(C_1-C_6)$alkyl$(C_5-C_9)$heteroaryl, $CONH(C_1-C_6)$alkyl$(C_5-C_9)$heteroaryl, and $CO_2(C_1-C_6)$alkyl$(C_5-C_9)$heteroaryl;

Y is $CH_2$ or O;

X is absent, O, $NR^4$, or $(C_1-C_4)$alkyl;

$R^4$ is H or $(C_1-C_6)$alkyl;

$R^5$ and $R^6$ at every occurrence are each independently selected from H, $(C_1-C_6)$alkyl, $(C_1-C_6)$haloalkyl, $(C_6-C_{10})$aryl, $(C_1-C_6)$alkyl$(C_6-C_{10})$aryl, $(C_2-C_9)$heterocycloalkyl, $(C_1-C_6)$alkyl$(C_2-C_9)$heterocycloalkyl, $(C_5-C_9)$heteroaryl, and $(C_1-C_6)$alkyl$(C_5-C_9)$heteroaryl, wherein any of the foregoing, except for H, is optionally substituted with one or more substituents;

m is 1 or 2; and

Z is selected from $(C_3-C_{10})$cycloalkyl, $(C_1-C_6)$alkyl$(C_3-C_{10})$cycloalkyl, $(C_2-C_9)$heterocycloalkyl, $(C_1-C_6)$alkyl$(C_2-C_9)$heterocycloalkyl, $(C_6-C_{10})$aryl, $(C_1-C_6)$alkyl$(C_6-C_{10})$aryl, $(C_5-C_9)$heteroaryl, and $(C_1-C_6)$alkyl$(C_5-C_9)$heteroaryl wherein any of the foregoing is optionally substituted with one or more substituents; or Z is $NR^8R^9$ wherein $R^8$ and $R^9$ are each independently selected from H, $(C_1-C_6)$alkyl, $(C_3-C_{10})$cycloalkyl, $(C_1-C_6)$alkyl$(C_3-C_{10})$cycloalkyl, $(C_6-C_{10})$aryl, $(C_1-C_6)$alkyl$(C_6-C_{10})$aryl, $(C_2-C_9)$heterocycloalkyl, $(C_1-C_6)$alkyl$(C_2-C_9)$heterocycloalkyl, $(C_5-C_9)$heteroaryl, and $(C_1-C_6)$alkyl$(C_5-C_9)$heteroaryl, wherein any of the foregoing, with the exception of H is optionally substituted with one or more substituents and provided that $R^8$ and $R^9$ are not both H; or $R^8$ and $R^9$ are taken together to form a $(C_2-C_9)$heterocycloalkyl ring that is optionally substituted with one or more substituents.

In some embodiments of Formula II:

Z is selected from $(C_3-C_{10})$cycloalkyl, $(C_1-C_6)$alkyl$(C_3-C_{10})$cycloalkyl, $(C_2-C_9)$heterocycloalkyl, $(C_1-C_6)$alkyl$(C_2-C_9)$heterocycloalkyl, $(C_6-C_{10})$aryl, $(C_1-C_6)$alkyl$(C_6-C_{10})$aryl, $(C_5-C_9)$heteroaryl, and $(C_1-C_6)$alkyl$(C_5-C_9)$heteroaryl wherein any of the foregoing is optionally substituted with one or more substituents.

In other embodiments of Formula II:

$R^3$ is selected from H, $(C_1-C_6)$alkyl, $(C_1-C_6)$hydroxyalkyl, $(C_1-C_6)$haloalkyl, $(C_1-C_6)$alkyl$(C_1-C_6)$alkoxy, $(C_6-C_{10})$aryl, $(C_1-C_6)$alkyl$(C_6-C_{10})$aryl, $(C_3-C_{10})$cycloalkyl, $(C_1-C_6)$alkyl$(C_3-C_{10})$cycloalkyl, $(C_2-C_9)$heterocycloalkyl, $(C_1-C_6)$alkyl$(C_2-C_9)$heterocycloalkyl, and $(C_5-C_9)$heteroaryl, wherein any of the foregoing, except for H, is optionally substituted with one or more substituents.

In further embodiments of Formula II:

Z is $(C_6-C_{10})$aryl or $(C_5-C_9)$heteroaryl wherein either of the foregoing is optionally substituted with between one or more substituents.

In still other embodiments of Formula II:

p and q are each 0.

In yet other embodiments of Formula II:

X is absent;

$R^3$ is selected from H, $(C_1-C_6)$alkyl, $(C_1-C_6)$hydroxyalkyl, $(C_1-C_6)$haloalkyl, $(C_1-C_6)$alkyl$(C_1-C_6)$alkoxy, $(C_6-C_{10})$aryl, $(C_1-C_6)$alkyl$(C_6-C_{10})$aryl, $(C_3-C_{10})$cycloalkyl, $(C_1-C_6)$alkyl$(C_3-C_{10})$cycloalkyl, $(C_2-C_9)$heterocycloalkyl, $(C_1-C_6)$alkyl$(C_2-C_9)$heterocycloalkyl, and $(C_5-C_9)$heteroaryl, wherein any of the foregoing, except for H, is optionally substituted with one or more substituents; and Z is selected from $(C_3-C_{10})$cycloalkyl, $(C_1-C_6)$alkyl$(C_3-C_{10})$cycloalkyl, $(C_2-C_9)$heterocycloalkyl, $(C_1-C_6)$alkyl$(C_2-C_9)$heterocycloalkyl, $(C_6-C_{10})$aryl, $(C_1-C_6)$alkyl$(C_6-C_{10})$aryl, $(C_5-C_9)$heteroaryl, and $(C_1-C_6)$alkyl$(C_5-C_9)$heteroaryl wherein any of the foregoing is optionally substituted with one or more substituents.

In still other embodiments, compounds of Formula II include all compounds specifically named herein.

Another aspect of this application is directed to compounds of Formula I having the structure of Formula III:

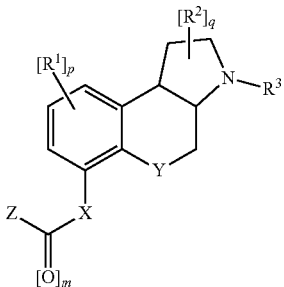

III or salts thereof.

Another aspect of this application is directed to compounds of Formula I having the structure of Formula IV:

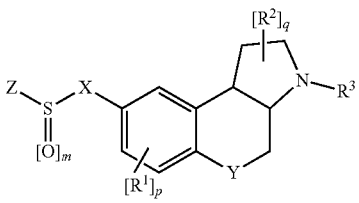

IV or salts thereof.

Further aspects of this application are directed toward compounds of Formula I having the structure of Formula V:

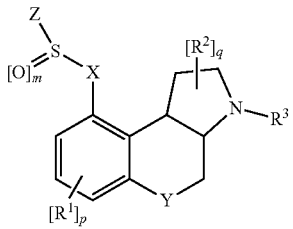

V or salts thereof.

In another aspect, this application relates to synthetic intermediates and methods of making compounds of Formula I.

In another aspect, this application relates to salts of the compounds of Formula I wherein the salts are pharmaceutically acceptable salts.

In another aspect, this application relates to compositions comprising one or more compounds of Formula I or a salt thereof. In certain specific embodiments, the salt is a pharmaceutically acceptable salt. In additional specific embodiments, the composition further comprises at least one pharmaceutically acceptable excipient. In other specific embodiments, the composition further comprises at least one additional therapeutically active agent.

In another aspect, this application relates to methods of treating conditions, disorders or diseases mediated, controlled, effected or influenced by a member of the serotonin receptor (5-HT) family. In some embodiments, the condition, disorder or disease is mediated, controlled, effected or influenced by at least one of the $5\text{-}HT_6$ or $5\text{-}HT_7$ receptors. In some specific embodiments, the condition, disorder or disease is: related to the central nervous system (CNS) such as memory disorders, anxiety, epilepsy, migraine, panic attacks, depression, bipolar disorder, obsessive compulsive disorders, cognition/cognitive disorders, mild cognitive impairment (MCI), senile dementia, psychosis, schizophrenia, ADHD/ADD; or for the treatment of pain including neuropathic pain and chronic pain; head trauma or injury; or for the treatment of neurodegenerative conditions, disorders or diseases such as Alzheimer's disease, Parkinson's disease, Huntington's disease, amyotrophic lateral sclerosis (ALS) or multiple sclerosis; or for the treatment of conditions, disorders or diseases related to addiction and/or withdrawal from substances such as narcotics, ethanol (alcoholism), nicotine, and/or benzodiazepines; sleep/wakefulness disorders; or for the treatment of gastrointestinal (GI) conditions, disorders or diseases such as irritable bowel syndrome (IBS), functional bowel disorder; or for the treatment of conditions, disorders or diseases related to feeding behaviors or food intake such as anorexia, cachexia, and obesity.

In another aspect this application relates to methods for improving cognition (cognitive enhancement) and/or improving memory in otherwise healthy subjects.

In another aspect, this application relates to methods of treating conditions, disorders or diseases mediated, controlled, effected or influenced by the $5\text{-}HT_6$ receptor comprising administering a therapeutically effective amount of a compound of Formula I or a pharmaceutically acceptable salt thereof. In some specific embodiments, the method further comprises administration of at least one additional therapeutically active agent.

DEFINITIONS

The compounds and intermediates described herein may be named according to either the IUPAC (International Union for Pure and Applied Chemistry) or CAS (Chemical Abstracts Service) nomenclature systems.

The various hydrocarbon-containing moieties described herein may be described using a prefix designating the minimum and maximum number of carbon atoms in the moiety, i.e. "$(C_a\text{-}C_b)$". For example, $(C_a\text{-}C_b)$alkyl indicates an alkyl moiety of the integer "a" to the integer "b" carbon atoms, inclusive. Certain moieties may also be described according to the minimum and maximum number of members with or without specific reference to a particular atom or group of atoms. For example, the terms "a- to b-membered" or "having between a to b members" or "between a to b substituents" respectively refer to a moiety having the integer "a" to the integer "b" number of atoms or substituents, inclusive.

As used herein by themselves or in conjunction with another term or terms, "alkyl" and "$(C_1\text{-}C_6)$alkyl" refer to straight or branched hydrocarbon groups containing the requisite number of carbon atoms as described above. As used herein, alkyl groups may be optionally substituted with between one to four substituents. Representative examples of alkyl groups include, but are not limited to, e.g., methyl, ethyl, n-propyl, isopropyl, n-butyl, isobutyl, sec-butyl, t-butyl, etc.

As used herein by themselves or in conjunction with another term or terms, "alkoxy" and "$(C_1\text{-}C_6)$alkoxy" refer to straight or branched hydrocarbon groups containing the requisite number of carbon atoms as described above, bonded to an oxygen atom. As used herein, all such alkoxy groups may be optionally substituted with between one to four substituents. Representative examples of alkoxy groups include, but are not limited to, e.g. methoxy, ethoxy, tert-butoxy, etc.

As used herein by themselves or in conjunction with another term or terms, "aminoalkyl" and "$(C_1-C_6)$aminoalkyl" refer to alkyl groups, as described above, where at least one hydrogen atom, at any position, is replaced by an amino group, i.e., $NH_2$. As used herein, aminoalkyl groups may be optionally substituted with between one to four substituents.

As used herein by themselves or in conjunction with another term or terms, "alkenyl" and "$(C_1-C_6)$alkenyl" refer to straight or branched hydrocarbon groups containing the requisite number of carbon atoms as described above, and at least one double bond. As used herein, alkenyl groups may be optionally substituted with between one to four substituents. Representative examples of alkenyl groups include, but are not limited to, e.g. ethenyl, 2-propenyl (allyl), iso-propenyl, 2-methyl-1-propenyl, etc.

As used herein by themselves or in conjunction with another term or terms, "alkynyl" and "$(C_1-C_6)$alkynyl" refer to straight or branched hydrocarbon groups containing the requisite number of carbon atoms as described above, and at least one triple bond. As used herein, alkynyl groups may be optionally substituted with between one to four substituents. Representative examples of alkynyl groups include, but are not limited to, e.g. ethynyl, propynyl, butynyl, etc.

As used herein by itself or in conjunction with another term or terms, "aromatic" refers to monocyclic and polycyclic conjugated ring systems containing 4n+2 pi electrons, where n is an integer. As used herein, aromatic refers to and includes ring systems that contain only carbon atoms (i.e. "aryl" or "aromatic carbocycle") as well as ring systems that contain at least one heteroatom selected from N, O or S (i.e. "heteroaromatic" or "heteroaryl"). As used herein, all such aromatic ring systems may be optionally substituted with between one to four substituents.

As used herein by itself or in conjunction with another term or terms, "non-aromatic" refers to a monocyclic or polycyclic ring system having at least one isolated, i.e. not part of a conjugated pi system, double bond. As used herein, non-aromatic refers to and includes ring systems that contain only carbon atoms as well as ring systems that contain at least one heteroatom selected from N, O or S, such as for example, 1,2,5,6-tetrahydropyridine. As used herein, all such non-aromatic ring systems may be optionally substituted with between one to four substituents.

As used herein by themselves or in conjunction with another term or terms, "aryl" and "$(C_6-C_{10})$aryl" refer to monocyclic and polycyclic hydrocarbon ring systems, i.e. carbocycles, having the requisite number of carbon atoms as described above, where at least one ring is aromatic, as described above. As used herein, aryl groups may be optionally substituted with between one to four substituents. Representative examples include, but are not limited to, e.g., phenyl (phenylenyl), napthyl (napthylenenyl), 1,2,3,4-tetrahydro-naphthalenyl, etc.

As used herein by themselves or in conjunction with another term or terms, "arylalkyl" and "$(C_1-C_6)$alkyl$(C_6-C_{10})$aryl" refer to alkyl groups, as defined above, having an aryl group, as defined above, as a substituent. Arylalkyl groups may be optionally substituted with between one to four substituents. Representative examples include, but are not limited to, e.g., benzyl, phenylethyl, etc.

As used herein by themselves or in conjunction with another term or terms, "aryloxy", "$(C_6-C_{10})$aryloxy", "alkoxyaryl", and "$(C_1-C_6)$alkoxy$(C_6-C_{10})$aryl" refer to aryl groups, as defined above, that are bonded directly to an oxygen atom or to an alkoxy group, as defined above, respectively. These groups may be optionally substituted with between one to four substituents. Representative examples include, but are not limited to, e.g., phenoxy, benzyloxy, phenylethoxy, napthyloxy, etc.

As used herein by themselves or in conjunction with another term or terms, "carbocyclic" and "carbocycle" refer to monocyclic and polycyclic ring systems that contain only carbon atoms in the ring(s),i.e. hydrocarbon ring systems, without regard to aromaticity. Thus, carbocyclic and carbocycle refer to and include ring systems that are saturated or unsaturated, aromatic or non-aromatic, as well as ring systems having fully saturated, aromatic and/or non-aromatic portions. The terms carbocyclic and carbocycle further include bridged, fused, and spirocyclic ring systems. Carbocycles may be optionally substituted with between one to four substituents. Representative examples include, but are not limited to, e.g., cyclopropyl, cyclobutyl, 1,3-dimethylcyclopentyl, cyclohexyl, phenyl, napthyl, cyclohexenyl, 2,3-dihydro-indenyl, 1,2,3,4-tetrahydro-naphthalene, spiro[3.4]octanyl, bicycle[2.2.1]hept-5-enyl, adamantanyl, norbornanyl, bicyclo[2.2.1]heptanyl, etc.

As used herein by themselves or in conjunction with another term or terms, "halo" and "halogen" include fluorine, chlorine, bromine, and iodine atoms and substituents. These groups may also be referred to as fluoro, chloro, bromo and iodo.

As used herein by themselves or in conjunction with another term, "haloalkyl" and "$(C_1-C_6)$ haloalkyl" refer to alkyl groups, as defined above, having one or more hydrogen atoms replaced by halogen atoms, as defined above. It should be understood that where there is more than one halogen atom present in a haloalkyl group, the halogen atoms may be the same or different and/or may be located on the same carbon atom or on different carbon atoms. Representative examples of haloalkyl groups include, but are not limited to, e.g., difluoromethyl, trifluoromethyl, chloromethyl, 3-bromo-2-chloro-propyl, 2,2-dibromoethyl, 2-bromo-2-chloro-ethyl, 1,1,2,2,3,3,4,4-octafluoro-butyl, etc.

As used herein by themselves or in conjunction with another term or terms, "haloalkoxy" and "$(C_1-C_6)$haloalkoxy" refer to haloalkyl groups, as defined above, bonded to an oxygen atom. Representative examples of haloalkoxy groups include, but are not limited to, e.g., difluoromethoxy, trifluoromethoxy, chloromethoxy, 2,2-dibromoethoxy, 3-bromo-2-chloro-propoxy, 1,1,2,2,3,3,4,4-octafluoro-butoxy, etc.

As used herein by themselves or in conjunction with another term or terms, "cycloalkyl" and "$(C_3-C_{10})$cycloalkyl" refer to monocyclic and polycyclic hydrocarbon ring systems containing the requisite number of carbon atoms as described above, which may be optionally substituted with between one to four substituents. These terms refer to and include ring systems that are fully saturated or contain at least one double or triple bond, as well as ring systems with fully saturated or aromatic or non-aromatic portions, such as, for example, 1,2,3,4-tetrahydro-naphthalenyl. It should be understood that these terms further refer to and include bridged and/or fused polycyclic structures such as, for example, bicyclo[3.2.1]octanyl, bicyclo[5.2.0]nonanyl, bicyclo[2.2.1]hept-5-enyl and the like, as well as spirocyclic ring systems such as, for example, spiro[3.4]octanyl, spiro[3.5]nonyl and the like. Other representative examples of cycloalkyl groups include, but are not limited to, e.g., cyclopropyl, methylcyclopropyl, cyclobutyl, cyclobutenyl, isopropylcyclobutyl, cyclopentyl, 1,3-dimethylcyclopentyl, cyclohexyl, cyclohexenyl, cycloheptyl, 2,3-dihydro-1H-inden-2-yl, norbornyl, decahydronaphthalenyl, etc.

As used herein by themselves or in conjunction with another term or terms, "cycloalkyloxy", "$(C_3-C_{10})$cycloalkyloxy", "alkoxycycloalkyl", "alkoxy$(C_3-C_{10})$cycloalkyl", and "$(C_1-C_6)$alkoxy$(C_3-C_{10})$cycloalkyl" refer to a cycloalkyl group having the requisite number of carbon atoms as described above, bonded directly to an oxygen atom or an alkoxy group, respectively. As used herein, these groups may be optionally substituted with between one to four substituents. Representative examples include, but are not limited to, e.g., cyclopropyloxy, cyclobutyloxy, cyclopentyloxy, 2-cyclopentyl-ethoxy, cyclohexyl-methoxy, cyclohex-3-yloxy, etc.

As used herein by themselves or in conjunction with another term or terms, "heterocycloalkyl", "$(C_2-C_9)$heterocycloalkyl", "heterocycle", and "heterocyclic" refer to monocyclic and polycyclic ring systems containing the requisite number of carbon atoms as described above and at least one heteroatom selected from N, O, or S. These groups may be optionally substituted with between one to four substituents. These terms further refer to and include ring systems that are fully saturated or contain at least one double or triple bond, as well as ring systems with fully saturated or aromatic portions, such as for example, dihydrobenzo[1,4]-dioxinyl, and/or non-aromatic portions. It should be understood that polycyclic heterocycloalkyl groups further include fused, bridged and spirocyclic ring systems and ring systems in which the N or S is oxidized, i.e. 1,1-dioxide-thiomorpholinyl, 1-oxo-piperidinyl. Additional representative examples of heterocycloalkyl groups include, but are not limited to, e.g., oxiranyl, thiaranyl, aziridinyl, oxetanyl, thiatanyl, azetidinyl, tetrahydrofuranyl, tetrahydrothiophenyl, pyrrolidinyl, dihydrofuranyl, tetrahydropyranyl, pyranyl, tetrahydrothiopyranyl, thiopyranyl, piperidinyl, 1,4-dioxanyl, 1,4-oxathianyl, morpholinyl, thiomorpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thieazepanyl, 1,4-diazepanyl, 1,2-tetrahydrothiazin-2-yl, 1,3-tetrahydrothiazin-3-yl, tetrahydrothiadiazinyl, 1,2-tetrahydrodiazin-2-yl, 1,3-tetrahydrodiazin-1-yl, tetrahydroazepinyl, chromanyl, chromenyl, isoxazolidinyl, 1,3-oxazolidin-3-yl, isothiazolidinyl, 1,3-thiazolidin-3-yl, 1,2-pyrazolidin-2-yl, 1,3-pyrazolidin-1-yl, 7-oxa-1-aza-spiro[4.4]nonanyl, 3-azabicyclo[3.1.0]hexanyl, indolinyl, octahydro-1H-indolyl, octahydro-2H-pyrido[1,2-a]pyrazinyl, 3-azabicyclo[4.1.0]heptanyl, 3,4-dihydro-2H-pyranyl, 1,2,3,4-tetrahydropyridinyl, etc.

As used herein by themselves or in conjunction with another term or terms, "alkylheterocycloalkyl" and "$(C_1-C_6)$ alkyl$(C_2-C_9)$heterocycloalkyll" refer to alkyl groups, as defined above, having a heterocycloalkyl group, as defined above, as a substituent. Alkylheterocycloalkyl groups may be optionally substituted with between one to four substituents. Representative examples include, but are not limited to, e.g., piperidinylmethyl, pyrrolidinylethyl, etc.

As used herein by themselves or in conjunction with another term or terms, "heterocycloalkyloxy", "$(C_2-C_9)$heterocycloalkyloxy", "alkoxy$(C_2-C_9)$heterocycloalkyl" and "$(C_1-C_6)$alkoxy$(C_2-C_9)$heterocycloalkyl" respectively refer to a heterocycloalkyl group, as defined above, bonded directly to an oxygen atom or to an alkoxy group, as defined above, and may be optionally substituted with between one to four substituents. Representative examples include, but are not limited to, e.g., pyrrolidin-3-yloxy, piperidin-4-yloxy, azepan-4-yloxy, pyrrolidin-1-yl-ethoxy, pyrrolidin-2-yl-methoxy, tetrahydro-pyran-3-ylpropyloxy, etc.

As used herein by themselves or in conjunction with another term or terms, "heteroaryl", "$(C_5-C_9)$heteroaryl", and "heteroaromatic", refer to monocyclic and polycyclic aromatic ring systems containing the requisite number of carbon atoms, as described above, and at least one heteroatom selected from N, O, or S. As used herein, a heteroaromatic ring system refers to and includes polycyclic ring systems that contain aromatic portions while other portions of the ring system may be fully saturated or non-aromatic such as, for example, dihydrobenzo[1,4]-dioxinyl. Heteroaromatic rings may be optionally substituted with between one to four substituents. Additional representative examples include, but are not limited to, e.g., pyrrolyl, furanyl, thiophenyl, thienyl, pyrazolyl, imidazolyl, isoxazolyl, oxazolyl, isothiazolyl, thiazolyl, 1,2,3-triazolyl, 1,2,4-triazolyl, tetrazolyl, 1,3,5-oxadiazolyl, 1,2,4-oxadiazolyl, 1,2,3-oxadiazolyl, 1,3,5-thiadiazolyl, 1,2,3-thiadiazolyl, 1,2,4-thiadiazolyl, pyridinyl (pyridyl), pyridazinyl, pyrimidinyl, pyrazinyl, 1,2,3-triazinyl, 1,3,5-triazinyl, pyrazolo[3,4-b]pyridinyl, cinnolinyl, pteridinyl, purinyl, 6,7-dihydro-5H-[1]pyrindinyl, benzo[b]thiophenyl, 5,6,7,8-tetrahydro-quinolin-3-yl, benzoxazolyl, benzothiazolyl, benzisothiazolyl, benzisoxazolyl, benzimidazolyl, thianaphthenyl, isothianaphthenyl, benzofuranyl, isobenzofuranyl, isoindolyl, indolyl, indolizinyl, indazolyl, isoquinolyl, quinolyl, phthalazinyl, quinoxalinyl, quinazolinyl, benzoxazinyl, 1,2,3,4-tetrahydro-isoquinolinyl, 2,3-dihydro-1H-isoindolyl, 1,3,4,5-tetrahydro-benzo[b]azepin-2-one, 1,3,4,5-Tetrahydro-benzo[d]azepin-2-one, 2,3,4,5-Tetrahydro-benzo[c]azepin-1-one, 1,2,4,5-Tetrahydro-benzo[c]azepin-3-one, 2,3,4,5-Tetrahydro-1H-benzo[b]azepinyl, 2,3,4,5-Tetrahydro-1H-benzo[d]azepinyl, 2,3,4,5-Tetrahydro-1H-benzo[c]azepinyl, etc.

As used herein, "∼" indicates a point of attachment.

As used herein by itself or in conjunction with another term or terms, "pharmaceutically acceptable" indicates that the designated entity such as for example, e.g. carrier, vehicle, diluent, excipient, salt or prodrug, is generally chemically and/or physically compatible with the other ingredients comprising a formulation, and/or is generally physiologically compatible with the recipient thereof.

As used herein by themselves or in conjunction with another term or terms, "subject(s)" and "patient(s)", refer to mammals, including humans.

As used herein by itself or in conjunction with another term or terms, "substituted" indicates that a hydrogen atom on a molecule has been replaced with a different atom or group of atoms and the atom or group of atoms replacing the hydrogen atom is a "substituent." It should be understood that the terms "substituent", "substituents", "moiety", "moieties", "group", or "groups" refer to substituent(s) when used in conjunction with the phrase " . . . optionally substituted by between one to four . . . " unless otherwise specified.

As used herein, representative examples of substituents include, but are not limited to, e.g., hydrogen (may be denoted as H), halogen (may be denoted as halo), $(C_1-C_6)$alkyl, $(C_1-C_6)$alkoxy, $(C_1-C_6)$alkoxy$(C_1-C_4)$alkyl, carboxylic acid (may be denoted as COOH), formyl, $(C_1-C_6)$acyl, $(C_1-C_6)$haloalkyl, $(C_1-C_6)$haloalkoxy, hydroxyl (may be denoted as OH), $(C_1-C_6)$aminoalkyl, $C_1-C_6)$hydroxyalkyl, nitro (may be denoted as $NO_2$), cyano (may be denoted as CN), amino (may be denoted as $NH_2$), mono- or di-$(C_1-C_6)$alkylamino (may be denoted as $NHR^1$, $NR^1R^2$ or $N(R^1)_2$, oxo (may be denoted as >=O or carbonyl), $(C_6-C_{10})$aryl, $(C_1-C_6)$alkyl$(C_6-C_{10})$aryl, $(C_6-C_{10})$aryloxy, $(C_1-C_6)$alkoxy$(C_6-C_{10})$aryl, $(C_5-C_9)$heteroaryl, $(C_5-C_9)$heteroaryloxy, $(C_1-C_6)$alkyl$(C_5-C_9)$heteroaryl, $(C_1-C_6)$alkoxy$(C_5-C_9)$heteroaryl, $(C_1-C_6)$alkoxycarbonyl (may be denoted as COOR, OCOR, or $CO_2R$), $(C_3-C_{10})$cycloalkyl, $(C_3-C_{10})$cycloalkyloxy, $(C_3-C_{10})$cycloalkyl$(C_1-C_6)$alkoxy, $(C_1-C_6)$alkyl$(C_3-C_{10})$cycloalkyl, $(C_2-C_9)$ heterocycloalkyl, $(C_2-C_9)$heterocycloalkyloxy, $(C_1-C_6)$alkyl $(C_2-C_9)$heterocyclalkyl, $(C_1-C_6)$alkoxy$(C_2-C_9)$ heterocycloalkyl, $(C_1-C_6)$alkyl$(C_1-C_6)$alkoxycarbonyl (may be denoted as RCOOR, ROCOR, or $RCO_2R$), $(C_1-C_6)$alkylsulfinyl, $(C_1-C_6)$alkylsulfonyl, mono- and di-$(C_1-C_6)$alkylaminocarbonyl (may be denoted as $NH_2CO$, NHCO, $NR^1CO$, $N(R^1)_2CO$), $(C_1-C_6)$acylthio, and $(C_1-C_6)$acyloxy.

As used herein, "treating", "treated", and "treatment", whether used alone or in conjunction with another term or terms, include preventative (e.g., prophylactic), ameliorative, palliative, and curative uses and results, or any combination thereof. It should be understood that the terms "preventing" and "preventative" and "prophylactic" are not absolute but rather refer to uses and results where the administration of a compound or composition diminishes the likelihood or seriousness of a condition, symptom, or disease state, and/or delays the onset of a condition, symptom, or disease state for a period of time.

As used herein, the terms "therapeutic" and "therapeutically effective amount", whether used alone or in conjunction with another term or terms, denote an amount of a compound, composition or medicament that (a) treats or prevents a particular disease, condition or disorder; (b) attenuates, ameliorates or eliminates one or more symptoms of a particular disease, condition or disorder; (c) prevents or delays the onset of one or more symptoms of a particular disease, condition or disorder described herein. It should be understood that the terms "therapeutic" and "therapeutically effective" encompass any one of the aforementioned effects (a)-(c), either alone or in combination with any of the others (a)-(c).

As used herein, a "therapeutically active agent", whether used alone or in conjunction with another term or terms, refers to any compound, i.e. a drug, that has been found to be useful in the treatment of a disease or disorder and is not described by Formula I.

The compounds (including final products and intermediates) described herein may be isolated and used per se or may be isolated in the form of a salt. It should be understood that the terms "salt(s)" and "salt form(s)" used by themselves or in conjunction with another term or terms encompasses all inorganic and organic salts, including industrially acceptable salts, as defined herein, and pharmaceutically acceptable salts, as defined herein, unless otherwise specified. As used herein, industrially acceptable salts are salts that are generally suitable for manufacturing and/or processing (including purification) as well as for shipping and storage, but may not be salts that are typically administered for clinical or therapeutic use. Industrially acceptable salts may be prepared on a laboratory scale, i.e. multi-gram or smaller, or on a larger scale, i.e. up to and including a kilogram or more. Pharmaceutically acceptable salts, as used herein, are salts that are generally chemically and/or physically compatible with the other ingredients comprising a formulation, and/or are generally physiologically compatible with the recipient thereof. Pharmaceutically acceptable salts may be prepared on a laboratory scale, i.e. multi-gram or smaller, or on a larger scale, i.e. up to and including a kilogram or more. It should be understood that pharmaceutically acceptable salts are not limited to salts that are typically administered or have been approved (by a regulatory authority such as FDA) for clinical or therapeutic use in humans. A practitioner of ordinary skill will readily appreciate that some salts are both industrially acceptable as well as pharmaceutically acceptable salts. It should be understood that all such salts, including mixed salt forms, are within the scope of the application.

In general, salts of the present application can be prepared in situ during the isolation and/or purification of a compound (including intermediates), or by separately reacting the compound (or intermediate) with a suitable organic or inorganic acid or base (as appropriate) and isolating the salt thus formed. The degree of ionisation in the salt may vary from completely ionised to almost non-ionised. In practice, the various salts may be precipitated (with or without the addition of one or more co-solvents and/or anti-solvents) and collected by filtration or the salts may be recovered by evaporation of solvent(s). Salts of the present application may also be formed via a "salt switch" or ion exchange/double displacement reaction, i.e. reaction in which one ion is replaced (wholly or in part) with another ion having the same charge. One skilled in the art will appreciate that the salts may be prepared and/or isolated using a single method or a combination of methods.

Representative salts include, but are not limited to, acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate and the like. Other examples of representative salts include alkali or alkaline earth metal cations such as sodium, lithium, potassium, calcium, magnesium, and the like, as well as non-toxic ammonium, quaternary ammonium and amine cations including, but not limited to, ammonium, tetramethylammonium, tetraethylammonium, lysine, arginine, benzathine, choline, tromethamine, diolamine, glycine, meglumine, olamine and the like.

Certain compounds of Formula I may have two or more asymmetric centers and therefore can exist in a number of stereoisomeric configurations. Consequently, such compounds can be synthesized and/or isolated as mixtures of enantiomers and/or as individual (pure) enantiomers, as well as diastereomers and mixtures of different diastereomers. It should be understood that the present application includes all such enantiomers and diastereomers and mixtures thereof in all ratios.

In practice, resolution and isolation of pure enantiomers can be achieved using methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, the specific stereoisomers may be synthesized by using an optically active starting material, by asymmetric synthesis using optically active reagents, substrates, catalysts or solvents, or by converting one stereoisomer into the other by asymmetric transformation or inversion.

For those compounds of Formula I that contain one or more additional stereogenic centers, those skilled in the art will appreciate that all diastereoisomers and mixtures diastereoisomers in any amount of the compounds illustrated and discussed herein are within the scope of the present application.

Compounds of Formula I that exist as diastereoisomers may be isolated by methods known to those skilled in the art, for example, by crystallization, gas-liquid or liquid chromatography. Alternatively, intermediates in the course of a synthesis that exist as racemic mixtures may be subjected to resolution by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support with a bound chiral ligand or in the presence of a chiral solvent. It will be appreciated that where the desired stereoisomer is converted into another chemical entity by one of the separation procedures described above, a further step is required to liberate the desired enantiomeric form. Alternatively, specific stereoisomers may be synthesized by asymmetric synthesis using optically active reagents, substrates, catalysts or solvents, or by converting one stereoisomer into the other by asymmetric transformation or inversion.

Compounds of the application may be administered as prodrugs. The term "prodrug" refers to a compound that is transformed in vivo to yield a compound of Formula I. The in vivo transformation may occur by various mechanisms, such as hydrolysis, in the blood or other biological fluids.

A prodrug of a compound of Formula I may be formed in a conventional manner with one or more functional groups in the compound, such as an amino, hydroxyl or carboxyl group. For example, if a compound of Formula I contains a carboxylic acid functional group, a prodrug can comprise: (1) an ester formed by the replacement of a hydrogen of the acid group with a group such as ($C_1$-$C_6$)alkyl or ($C_6$-$C_{10}$) aryl; (2) an activated ester formed by the replacement of the hydrogen of the acid group with groups such as —($CR_2$)COOR', where $CR_2$ is a spacer and R can be groups such as H or methyl and R' can be groups such as ($C_1$-$C_6$)alkyl or ($C_6$-$C_{10}$) aryl; and/or (3) a carbonate formed by the replacement of the hydrogen of the acid with groups such as CHROCOR' where R can be groups such as H or methyl and R' can be groups such as ($C_1$-$C_6$)alkyl or ($C_6$-$C_{10}$)aryl. Similarly, if a compound of Formula I contains an alcohol functional group, a prodrug can be formed via the replacement of the hydrogen of the alcohol with groups such as ($C_1$-$C_6$)alkanoyloxymethyl or ($C_1$-$C_6$) alkanoyloxyaryl or by forming an ester via condensation with, for example, an amino acid. Where a compound of Formula I contains a primary or secondary amino group, a prodrug may comprise, for example, an amide formed by the replacement of one or both of the hydrogens of the amino group with ($C_1$-$C_{10}$)alkanoyl or ($C_6$-$C_{10}$)aroyl. Other prodrugs of amines are well known to those skilled in the art. Alternatively, certain compounds of Formula I may themselves act as prodrugs of other compounds of Formula I.

Discussions regarding prodrugs and their the use can be found in, for example, "Prodrugs as Novel Delivery Systems," T. Higuchi and W. Stella, Vol. 14 of the ACS Symposium Series, and *Bioreversible Carriers in Drug Design*, Pergamon Press, 1987 (ed. E B Roche, American Pharmaceutical Association). Further examples of replacement groups may be found in the aforementioned references.

This application is also directed to all isotopically-labeled compounds of Formula I. As used herein, the term "isotopically-labeled compound" refers to a compound that has been prepared such that at least one atom has been replaced by an atom having the same atomic number, but a different atomic mass or mass number.

Examples of isotopes that may be incorporated into compounds of Formula I include isotopes of: hydrogen, such as 2H and 3H; carbon, such as $^{11}$C, $^{13}$C and $^{14}$C; chlorine, such as $^{36}$Cl; fluorine, such as $^{18}$F; iodine, such as $^{123}$I and $^{125}$I; nitrogen, such as $^{13}$N and $^{15}$N; oxygen, such as $^{15}$O, $^{17}$O and $^{18}$O; phosphorus, such as $^{32}$P; and sulphur, such as $^{35}$S. It should be understood that a compound of Formula (I) may include isotopes of more than one element. For example, a compound of Formula (I) may include isotopes of both hydrogen and carbon.

Certain isotopically-labeled compounds of Formula I such as, for example, those incorporating a radioactive isotope, may be useful in drug and/or substrate tissue distribution or diagnostic studies. In particular, radioactive isotopes such as tritium, i.e. $^3$H, and carbon-14, i.e. $^{14}$C, are particularly useful for these purposes in view of their ease of incorporation and ready means of detection.

Other isotopically-labeled compounds of Formula I such as, for example, those incorporating deuterium, i.e. $^2$H, may have certain therapeutic advantages over unlabeled compounds of Formula (I). Under certain circumstances deuterium labeled compounds can exhibit greater metabolic stability, increased in vivo half-life and/or reduced dosage requirements as compared to the unlabeled version of the compound.

Incorporation of other isotopes, such as $^{11}$C, $^{18}$F, $^{15}$O and $^{13}$N, can be useful in Positron Emission Topography (PET) studies for examining substrate receptor occupancy.

One of ordinary skill in the art will readily appreciate additional advantages and applications of isotopically-labeled compounds of Formula I as being within the scope of the present disclosure.

Isotopically-labeled compounds of Formula I can generally be prepared by conventional techniques known to those skilled in the art or by processes analogous to those described in the accompanying Examples and Preparations using an appropriate isotopically-labeled reagents in place of the non-labeled reagent previously employed.

Preparations and Examples

In general, compounds of Formula I may be prepared by the methods described in the Preparations, Schemes, and Experimental sections of the present application and/or by additional or alternative processes and procedures known in the chemical arts in combination with the knowledge of the skilled practitioner. It should be understood that the methods set forth in the following descriptions, reaction Schemes, Preparations and Experimental sections are intended for illustrative purposes and are not to be construed as limiting the scope of the disclosure.

Alternative reagents, intermediates, starting materials, synthetic routes and methods can be used or adapted in practice, particularly in light of the scope of the present disclosure in combination with the knowledge of one of ordinary skill in the art. Such alternatives and modifications should be understood as being within the spirit and scope of the present application and the claims.

Unless otherwise indicated, it should be understood that variables appearing in or referred to in the Schemes, and/or Preparations are defined as above or as defined in the Claims.

Although specific embodiments and/or individual compounds will be described with reference to particular Schemes, Preparations, and/or Examples, it should be understood that these embodiments and/or compounds are illustrative of a small number (i.e. a subset) of the more general descriptions, genera, subgenera, formulae, species, embodiments and compounds that fall within the scope and spirit of the present application. Accordingly, these specific embodiments and/or compounds should not be interpreted as limiting the scope of the disclosure in any way.

General Synthesis

The following Schemes depict generalized routes that may be used to prepare the compounds described herein. Preparations (P01 through P08) describe particular reaction sequences that may be used to make various intermediates. The Examples provide additional detail regarding the synthesis of a number of intermediates and compounds of Formula I.

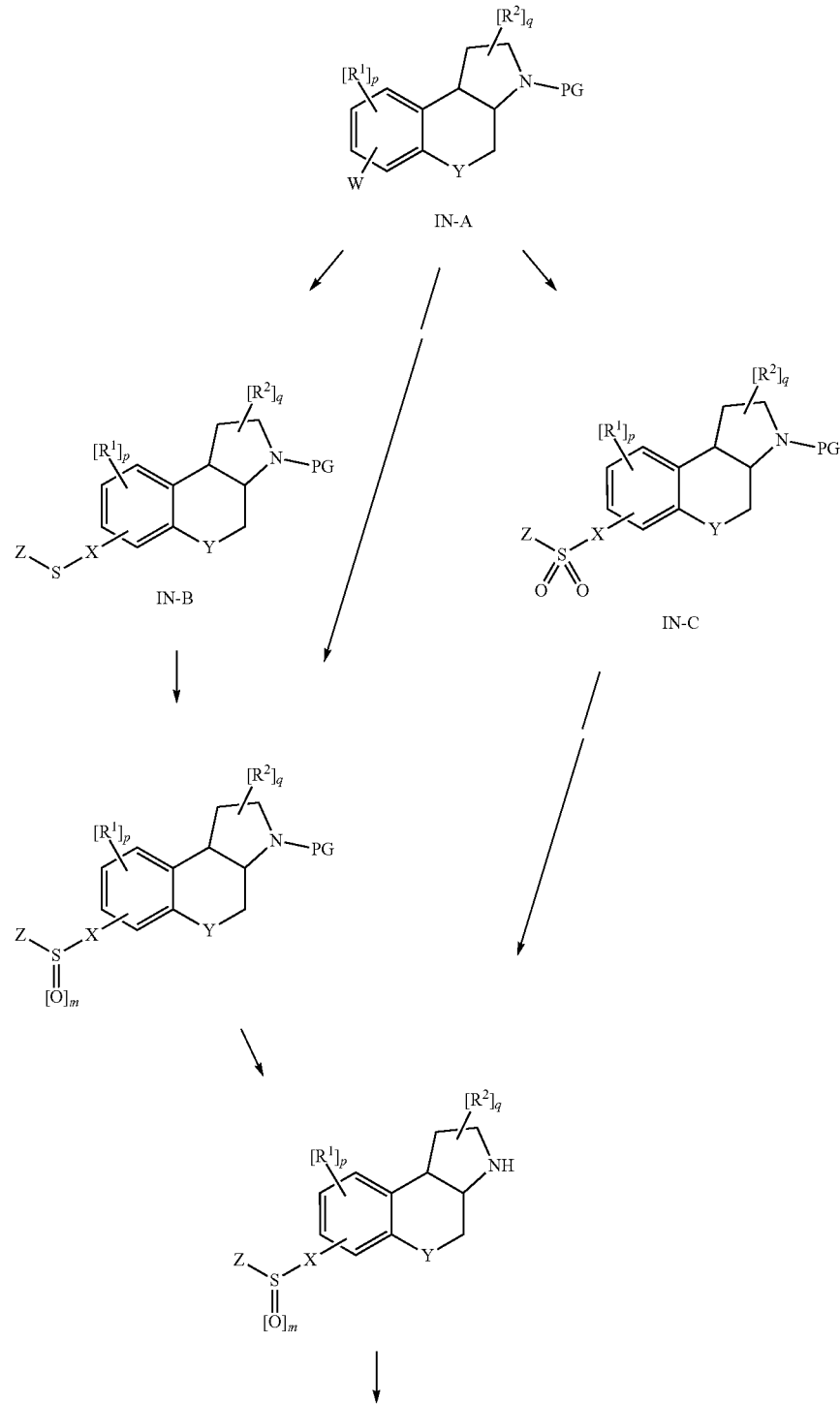

Scheme I

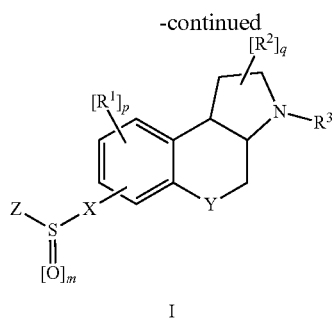

I

As shown in Scheme I compounds of Formula I may be prepared from an appropriately substituted tricyclic compound IN-A, where W represents a halogen, for example, chloride, bromide, or iodide, and PG denotes a protecting group. This intermediate may be coupled with a desired thiol (Z—SH) using Ullmann type reaction conditions to provide the corresponding thioether, IN-B. The Ullmann coupling can be affected using any number of methods and conditions known in the art. For example, the reaction may be conducted using a catalytic amount of CuI (copper iodide), in the presence of neocuproine (2,9-dimethyl-1,10-phenanthroline) or ethylene glycol, and a base, such as sodium tert-butoxide (NaOtBu), in an appropriate solvent, such as N,N-dimethylformamide (DMF) or toluene, at elevated temperatures, such as between about 70-100° C. Alternatively, the tricyclic halide may be converted to a trialkylsilyl thioether using a trialkylsilylthiol, such as triisopropylsilylthiol (TIPS-SH) in the presence of a palladium catalyst such as, tetrakis(triphenylphosphine)palladium(0) (Pd(PPh$_3$)$_4$) and a suitable base such as lithium hexamethyldisilazide (LHMDS) in a solvent such as dioxane at elevated temperatures. Treatment of the trialkylsilylthioether with a desired Z-Hal where Hal denotes a halide such as iodide, in the presence of CuI and cesium fluoride (CsF) in an appropriate solvent such as DMF provides the tricyclic thioether, IN-B.

The oxidation of IN-B with meta-chloroperoxybenzoic acid (mCPBA) or Oxone® in an appropriate solvent, such as methylene chloride (DCM) or tetrahydrofuran (THF) provides the corresponding sulfinyl/sulfonyl compound, i.e. where m is 1 or 2. Oxidation of IN-B with benzenesulfonyl-3-phenyl oxaziridine (Davis reagent) affords the corresponding sulfinyl compound, i.e., where m is 1.

Alternatively, IN-A can be converted to the sulfone directly using a desired sulfinic acid.

For compounds where W represents OH or NH$_2$, the corresponding sulfones, IN-C, i.e. where X is —O— or —NH—, may be accessed via reaction with the desired sulfonyl chloride, Z—SO$_2$Cl (not shown), in the presence of an appropriate base, such as cesium carbonate (Cs$_2$CO$_3$) or DIEA in a suitable solvent such as acetonitrile (MeCN or AcCN) or DMF, respectively. In practice these reactions may be conducted at elevated temperatures.

For compounds where W represents SO$_2$Cl, reaction with a desired alcohol, Z—OH (not shown) or a desired amine, R$^8$R$^9$N (not shown) provides the corresponding sulfone, IN-C. In practice, these reactions are conducted in the presence of a base, such as DIEA, in a suitable solvent such as DCM or DMF.

Cleavage of the protecting group (PG) may be affected using standard procedures well known in the art.

Introduction of R$^3$ may be accomplished using any number of standard procedures. For example, various R$^3$ groups may be introduced via N-alkylation using a desired halide, R$^3$—Hal (not shown), where Hal represents bromine or iodine in the presence of a suitable base such as N,N-diisopropylethylamine (DIEA) in an appropriate solvent such as DMF. In practice this reaction may be conducted at elevated temperatures. Other R$^3$ groups may be added via reductive animation with desired aldehydes or ketone, acylation with desired carboxamides, etc.

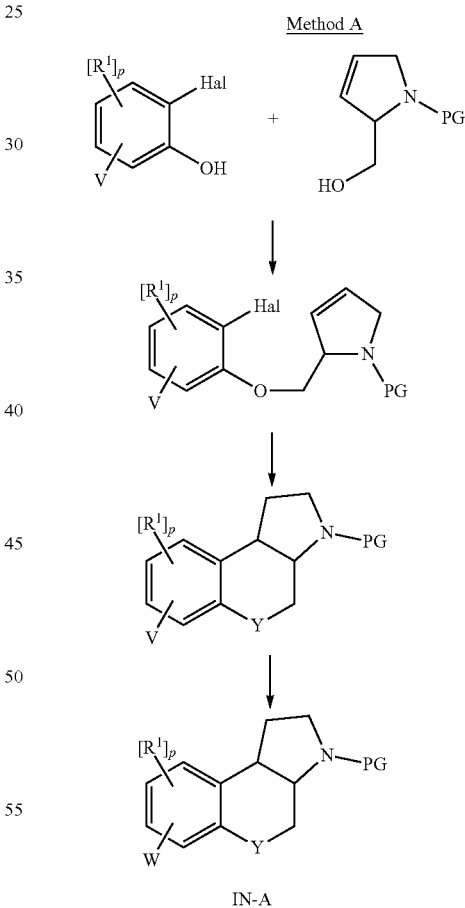

Method A

IN-A

Various intermediates of Formula IN-A may be prepared as shown in Method A. Coupling of an appropriately substituted halophenol, where V is a methoxy group and Hal represents either bromine or iodine, with N-protected pyrrol-2-yl methanol using Mitsunobu conditions provides the corresponding haloaryl ether. Typically, this coupling reaction proceeds in the presence of DEAD (diethyl azodicarboxylate) and triphenyl phosphine (P(Ph)$_3$), in a suitable solvent such as THF. In practice this reaction may be conducted at ambient temperature or below.

The resulting haloaryl ethers may be cyclized using tributyltin hydride (Bu$_3$SnH) in the presence of AIBN (2,2'-azobis (isobutyronitrile)) in a suitable solvent, such as toluene. In practice this reaction may be conducted at elevated temperatures and leads exclusively to the cis configuration at the ring juncture. Other conditions for affecting this transformation are known in the art. See for example, *Tetrahedron Letters*, 2001, 42, 6499-6502.

The tricyclic adduct, where V is methoxy, V may be converted to any number of functional groups using standard procedures known in the art. For example, treatment with boron tribromide (BBr$_3$) provides compounds where W is a hydroxide (—OH) which can in turn be converted to various amines, or a triflate. The triflate can in turn be converted to a halide such as iodide or bromine.

Standard procedures known in the art may also be used to introduce various functional groups into tricyclic adducts where V is H. For example, V can be converted to the corresponding halide using procedures known in the art, or converted to a nitro group (NO$_2$). The nitro compound can be reduced to the corresponding amine using standard reduction procedures known in the art.

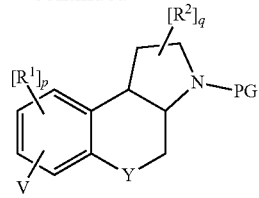

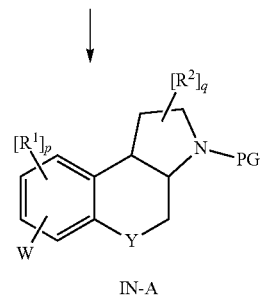

IN-A

Other intermediates of Formula IN-A may be accessed as shown in Method B using procedures and conditions known in the art. See for example, WO 96/31512, WO 97/47602 and US 2006-080752.

Other useful intermediates and derivatives not specifically described herein generally may be prepared from appropriately substituted materials using transformations and/or reaction sequences known in the art in combination with the knowledge of one of skill in the art. Such procedures and methods are described in reference books such as, for example, *Compendium of Organic Synthetic Methods*, Vols. I-VI (Wiley-Interscience) and elsewhere in the chemical literature.

One of skill in the art will appreciate that in some cases protecting groups may be required during a multi-step or single-step reaction sequence. In practice, a protecting group is used to mask or block a particular site/functional group in preparation for a chemical transformation at a different site/functional group in a molecule. After a particular target or transformation is complete or at some specific step later in a synthetic route, the protecting group can be removed using methods well know to those of ordinary skill in the art. The introduction, use and removal of protecting groups is thoroughly described in *Protective Groups in Organic Synthesis*, (3$^{rd}$ Ed., John Wiley & Sons, 1999).

Compositions

The compounds of Formula I and the pharmaceutically acceptable salts of such compounds may be administered as crystalline or amorphous materials, and may be administered alone or in combination with one or more of the other compounds described herein. In addition, compounds of Formula I and the pharmaceutically acceptable salts of such compounds may be administered in combination with one or more other therapeutically active agents. Generally, the compound(s) will be administered as a formulation, i.e. pharmaceutical composition, in association with one or more pharmaceutically acceptable excipients. The term "excipient" as used herein refers to any ingredient in the formulation other than the compound(s) of Formula I and any additional therapeutically active agent(s) as described above that may be present. Accordingly, excipient refers to and includes ingredients such as, for example: carriers, vehicles, solvents, adjuvants, lubricants, surfactants, binders, buffers, diluents, flavorings, coloring agents/dyes, disintegrants, emulsifying Method B

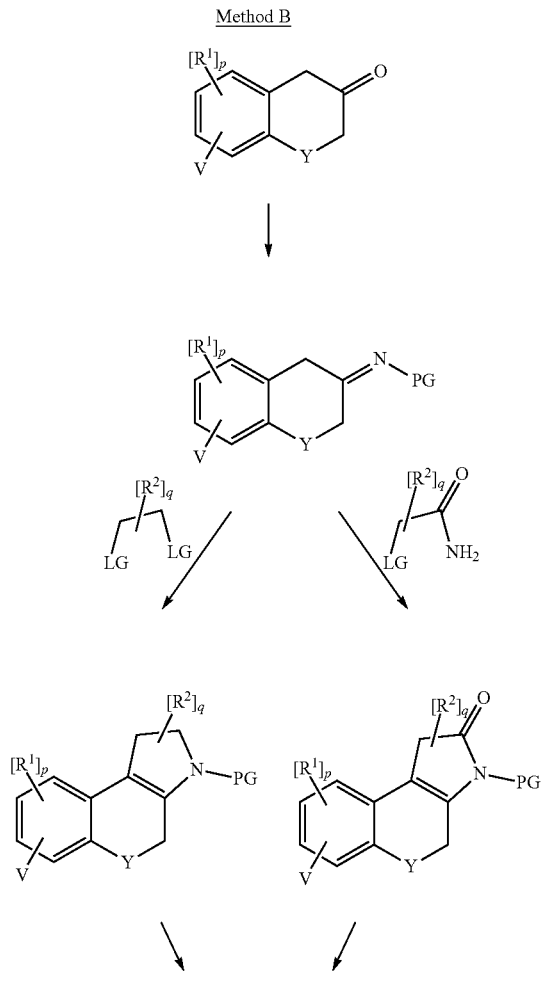

agents, suspending agents, plasticizers, solubilizers, fillers, bulking agents, and the like. The choice of excipient(s) will largely depend on factors such as: the particular mode of administration, the effect of the excipient(s) on solubility, stability, and release profile, and the nature of the dosage form. One skilled in the art will readily appreciate that this list of factors is not exhaustive. The compound(s) of the general Formula I and any additional therapeutically active agents (if present) may be generally referred to as the active ingredient(s) in a formulation or pharmaceutical composition.

Pharmaceutical compositions suitable for the delivery of compounds of Formula I and methods for their preparation will be readily apparent to those skilled in the art. Such compositions and methods for their preparation may be found, for example, in *Remington's Pharmaceutical Sciences*, 19th Edition (Mack Publishing Company, 1995).

The pharmaceutical composition may, for example, be in a form suitable for oral administration as a tablet, capsule (hard or soft filled), pill, powder, sustained or immediate release formulations, solution, suspension; for parenteral injection as a sterile solution, suspension or emulsion; or for topical administration as an ointment or cream. Additional dosage forms not specifically mentioned herein would be readily appreciated by one of ordinary skill in the art as being within the scope of the present application.

The relative amounts of the active ingredient(s) and the excipient(s) in a formulation or pharmaceutical composition will vary, depending upon the identity, size, and condition of the subject treated and further depending upon the route by which the composition is to be administered. By way of example, the composition may comprise between 0.1% and 100% (w/w) of active ingredient.

A pharmaceutical composition comprising one or more compounds of Formula I may be prepared, packaged, distributed, or sold in bulk, as a single unit dose, or as a plurality of single unit doses. As used herein, a "unit dose" is a discrete amount of a pharmaceutical composition comprising a predetermined amount of the active ingredient(s). The amount of the active ingredient(s) is generally equal to the dosage of the active ingredient(s) which would be administered to a subject or a convenient fraction of such a dosage such as, for example, one-half or one-third of such a dosage.

Dosing

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate pharmaceutical compositions in a unit dosage form for ease of administration and uniformity of treatment/therapeutic effect. As used herein, "unit dosage form" or "unit dose", by themselves or in combination with another term or terms, refer to the physically discreet amount(s) of medication, i.e. the active ingredient(s) in a pharmaceutical formulation, suitable for a one-time administration to the patient or subject to be treated; each unit dose containing a predetermined quantity of active compound(s) calculated to produce the desired therapeutic effect in association with the required pharmaceutical carrier. The more specific composition of the unit dosage forms comprising compounds of Formula I is dictated by and directly dependent on a number of variables, such as, for example: (a) the unique characteristics of the chemotherapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen is adjusted in accordance with methods well-known in the therapeutic arts. That is, the maximum tolerable dose can be readily established, and the effective amount for providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present invention.

It is to be noted that dosages and dosing regimens may vary with the type and severity of the condition to be alleviated, and may include the administration of single or multiple doses, i.e. QD (once daily), BID (twice daily), etc., over a particular period of time (days or hours). It is to be further understood that for any particular subject or patient, specific dosage regimens may need to be adjusted over time according to the individual need and the professional judgment of the person administering or supervising the administration of the pharmaceutical compositions. For example, doses may be adjusted based on pharmacokinetic or pharmacodynamic parameters, which may include clinical effects such as toxic effects and/or laboratory values. Thus, the present application encompasses intra-patient dose-escalation as determined by the skilled artisan. Procedures and processes for determining the appropriate dosage(s) and dosing regimen(s) are well-known in the relevant art and would readily be ascertained by the skilled artisan. As such, one of ordinary skill would readily appreciate and recognize that the dosage ranges set forth herein are exemplary only and are not intended to limit the scope or practice of the pharmaceutical compositions described herein.

Utility

This application relates to new compounds with affinity for the 5-$HT_6$ receptor, i.e., 5-$HT_6$ ligands, which may be useful as active ingredients in pharmaceutical preparations for the treatment of certain conditions, disorders or diseases related to the central nervous system (CNS) such as memory disorders, anxiety, epilepsy, migraine, panic attacks, depression, bipolar disorder, obsessive compulsive disorders, cognition/cognitive disorders, mild cognitive impairment (MCI), senile dementia, psychosis, schizophrenia, ADHD/ADD; or for the treatment of pain including neuropathic pain and chronic pain; head trauma or injury; or for the treatment of neurodegenerative conditions, disorders or diseases such as Alzheimer's disease, Parkinson's disease, Huntington's disease, amyotrophic lateral sclerosis (ALS) or multiple sclerosis; or for the treatment of conditions, disorders or diseases related to addiction or withdrawal from substances such as narcotics, ethanol, nicotine, and/or benzodiazepines; sleep/wakefulness disorders; or for the treatment of gastrointestinal (GI) conditions, disorders or diseases such as irritable bowel syndrome (IBS), functional bowel disorder; or for the treatment of conditions, disorders or diseases related to feeding behaviors or food intake such as anorexia, cachexia, and obesity.

These compounds may also be useful for the improvement of cognition (cognitive enhancement) and/or improvement of memory in otherwise healthy subjects.

Due to its unique localization in the central nervous system the 5-$HT_6$ receptor is an attractive target for the development of potential treatments for a variety of CNS-related conditions, disorders or diseases. A thorough overview of the distribution and characteristics of the 5-HT$_6$ receptor can be found in *Current Drug Targets—CNS & Neurological Disorders*, 2004, 3, 59-79.

There is a growing body of evidence that suggests that compounds with 5-HT$_6$ receptor affinity, in particular 5-HT$_6$ receptor antagonists, have potential therapeutic applications in the treatment of cognitive diseases, mild cognitive impairment (MCI), neurodegenerative diseases, schizophrenia, anxiety, and depression. See, for example, *Curr Top Med Chem*, 2008, 8, 1035-48 (5-HT$_6$ receptor antagonists and Alzheimer's disease); *Curr Opin Drug Discov Devel*, 2008, 11, 642-54 (5-HT$_6$ receptor antagonists and cognitive disorders); *Neuropsychobiolovy*, 2001, 43, 113-116 (serotonin-6 receptor polymorphism and schizophrenia); *Am. J. Med. Genet.*, 2000, 96, 217-221 (5-HT$_6$ receptor gene in bipolar affective disorder); *Neuropharmacoloqy*, 2007, 52, 1274-83 (5-HT$_6$ antagonist SB-399885 and animal models of anxiety and depression); *Pharmacology, Biochemistry, and Behavior*, 2005, 81, 673-82 (5-HT$_6$ receptor antagonists SB-357134 and SB-399885 and improvement in memory formation); *Pharmacol. Ther.*, 2005, 108, 320-333 (5-HT$_6$ receptors and cognitive enhancement); *Neurotherapeutics*, 2008, 5, 458-469 (5-HT$_6$ receptor antagonists as cognitive enhancing agents for Alzheimer's disease); *Expert Opin. Invest. Drugs*, 2002, 11, 457-467 (serotonin antagonists and depressive disorders).

Serotonin is also known to influence sleep, wakefulness and circadian rhythms, however the specific 5-HT receptor subtypes involved and their respective roles is still under investigation. 5-HT$_6$ receptors are associated with the hypothalamus, thalamus, and striatum in the brain. These regions are known to be important in the regulation of sleep and wakefulness and recent data in rats appears to confirm that 5-HT$_6$ receptors may be involved in sleep-wake regulation. *Sleep*, 2008, 31, 34-44. In this study, rats treated with RO 4368554, a 5-HT$_6$ receptor antagonist, experienced an increase in non-REM (non-rapid eye movement or NREM) sleep compared to an untreated control group. This observation indicates a possible connection between the 5-HT$_6$ receptor and sleep quality and/or sleep consolidation (i.e., the ability to maintain sleep continuously with minimal interruption), which in turn suggests a potential use of 5-HT$_6$ receptor antagonists in the treatment of sleep maintenance insomnia, i.e., the inability to maintain sleep throughout the night.

Association of the 5-HT$_6$ receptor and/or its mRNA in other areas of the brain, such as the cortex, amygdala, thalamus, periaqueductal grey, spinal cord and dorsal root ganglia implies a potential involvement of the 5-HT$_6$ receptor in pain and the modulation of nociceptive behaviour. The functional role of the 5-HT$_6$ receptor in nociception has been recently demonstrated in rats. See *European J. Pharmacol.*, 2007, 569, 59-63. In this study, SB-271046, a 5-HT$_6$ antagonist, appeared to have a short-lived, antinociceptive effect in a rat model of tonic, persistent pain. The data suggests that 5-HT$_6$ receptors can modulate the neural substrates involved in nociceptive processing.

The 5-HT$_6$ receptor has also generated a great deal of interest in connection with the treatment of food-intake or feeding related conditions or disorders. For example, chronic administration of 5-HT$_6$ receptor antisense oligionucleotides was found to significantly reduce food intake and body mass in rats. *J. Psychopharmacol.*, 1997, 11, A64. Other in vivo studies also indicate that 5-HT$_6$ antagonists influence feeding behaviour and body weight. See, e.g., *Br. J. Pharmacol.*, 1999, 126, 1537-1542; *Int. J. Obes.*, 2003, 27, Suppl. 1. Abst T1, 1-094; 34$^{th}$ *Annu. Meet. Soc. Neurosci. Abstract* 75.8. The results of these rat studies suggest that 5-HT$_6$ antagonists may reduce food intake by enhancing satiety. See *Drug Disc Today*, 2006, 11, 283-299; *Pharmacology & Therapeutics*, 2008, 117, 207-231.

A small clinical trial in man also appears to suggest that 5-HT$_6$ may have some influence in food intake or appetite. See, "Treatment of cancer-related anorexia with olanzapine and megestrol acetate: a randomized trial" in *Support Care Cancer*, published online, Sep. 11, 2009. In this study, olanzapine (OLN), a potent antagonist of the 5-HT$_6$ receptor, was administered in combination w/ megestrol acetate (MA) to patients with cancer-related anorexia (CRA). A second group of patients received only MA. Megestrol acetate is known to be at least partially effective as an appetite stimulant in cancer patients. However, the group of patients treated with the combination showed significant improvements in appetite, nausea, body weight, and quality of life (improvements in general activity, mood, work, walking, and enjoyment). Whether the 5-HT$_6$ receptor was a factor in the improvements reported in patients receiving the combination of OLN and MA is unclear, however, the authors hypothesize that the improvement in appetite in the combination treatment group could have been due to the improvement in mood. Other studies have shown that OLN as a single agent improves or reduces nausea in patients with advanced pain and cancer. See *J. Pain Symptom Manage.*, 2002, 23, 526-532; *J. Palliative Care*, 2003, 6, 251-255; *J. Pain Symptom Manage.*, 2003, 25, 587-582.

Another therapeutic use for 5-HT$_6$ antagonists may be for the treatment of addiction, such as for example substance and/or alcohol addiction (alcoholism), and in treating withdrawal from drug abuse in particular narcotics, alcohol (alcoholism), nicotine, and benzodiazepines. Novelty-seeking behavior in humans has long been associated with alcoholism and substance abuse. *Psychiatry Res*, 1979, 1, 255-264. Traditionally, novelty-seeking behavior has been linked to dopamine-mediated neurotransmission. However, there is evidence that behavioral responses to novelty may also be mediated by 5-HT. A reliable animal model of human novelty-seeking behavior that is highly predictive of drug use has been developed. This model and has recently been used to gain insight into the potential contribution of 5-HT$_6$ and 5-HT$_7$ receptors to novelty-seeking behavior and associated behaviors such as substance abuse. See *Neuropsychobioloqy*, 1996, 34, 136-145; *Exp. Clin. Psychopharmacol*, 2005, 13, 367-375.

The compounds described herein were tested for their ability to bind to the 5-HT$_6$ receptor. The ability of the compounds of the formula I to bind to the 5-HT$_6$ receptor may be measured using the assay and general procedures described below or by methods known in the art. The compounds of Formula I were generally found to be 5-HT$_6$ ligands, more specifically, the compounds of Formula I were generally found to be 5-HT$_6$ receptor antagonists.

In some embodiments, compounds of Formula I have an inhibition constant $K_i$ of the 5-HT$_6$ receptor of less than (<) 500 nM.

In other embodiments, compounds of Formula I have an inhibition constant $K_i$ to the 5-HT$_6$ receptor greater than (>) 500 nM but less than (<) 1000 nM.

In still other embodiments, compounds of Formula I have an inhibition constant $K_i$ to the 5-HT$_6$ receptor greater than (>) 1000 nM.

Human 5-HT$_6$ Receptor Binding Assay
Membrane Preparation

Membranes were prepared from CHO-K1 cells stably transfected with the human 5-HT$_6$ receptor (Euroscreen; ES-316-C). The cells were grown in Gibco Advanced DMEM-F12 (Cat#12634010) containing 2% dialyzed FBS (Hyclone Cat#SH30079.03). The cells were harvested in phosphate buffered saline (PBS) containing 0.1 mM EDTA and pelleted by centrifugation (1000×g), the supernatant was discarded and the pellets were stored at −80° C. prior to membrane preparation. Membranes were prepared as previously described (J Bio Chem. 1992, 267 (14) 9844-51). Briefly, frozen cell pellet was resuspended in a lysis buffer containing 5 mM Tris-HCl (pH 7.5), 5 mM EDTA and 1 complete EDTA-free protease inhibitor tablet (Roche Applied Science, Indianapolis, Ind.) per 50 mL buffer, and homogenized with a tissue homogenizer. The cell lysate was then centrifuged at 40,000×g for 30 min at 4° C. to collect the membranes. The membrane pellets were washed in membrane buffer (50 mM Tris-HCl (pH 7.5), 0.6 mM EDTA, 5 mM MgCl$_2$, 1 complete EDTA-free protease inhibitor tablet per 50 mL buffer) using a tissue homogenizer. The membranes were centrifuged at 40,000×g for 30 min at 4° C. and the pellets were resuspended in membrane buffer containing 250 mM sucrose, and protein concentration was determined using the Coomassie Plus kit (Pierce Biotechnology, Rockford, Ill.).

Receptor Binding Assays

Membranes prepared from cells expressing recombinant human 5-HT$_6$ receptor (h5-HT$_6$) were resuspended in assay buffer containing 50 mM Tris HCl, (pH7.4), 4 mM CaCl$_2$, 10 μg/mL saponin, and 0.1% (w/v) ascorbic acid. Membranes were preincubated using 1.75 μg membrane protein and 0.25 mg FlashBlue scintillation beads (PerkinElmer catalogue #FB001) per well at 4° C. for 30 min. Vehicle or test compound, and 4 nM [$^3$H]LSD (Perkin Elmer catalogue #NET638) were added and incubated for 3 hours at room temperature in a final volume of 80 μL in a 96-well plate. Test compounds or assay controls for total and non-specific binding were diluted in DMSO as 100× solutions and serially diluted by half log concentrations on a Perkin Elmer JANUS Automated Workstation. Serotonin (10 μM final concentration) was used to determine non-specific binding in the assay. Plates were read using the Microbeta Trilux 1450 LSC and luminescence counter. Data were analyzed by nonlinear repression using the dose-response equation (variable slope) to calculate IC$_{50}$ in XLfit4 (ID Business Solutions Inc.):

$$y = (\text{Bottom} + ((\text{Top} - \text{Bottom})/(1 + ((\text{IC}_{50}/x)\hat{}\,\text{Hill slope}))))$$

Binding of [$^3$H]LSD to the h5-HT$_6$ membranes was saturable with B$_{max}$=6.2 μmol/mg protein and K$_d$=2.3 nM. K$_i$ value was then calculated according to the Cheng-Prusoff method using the equation below (Cheng and Prusoff, 1973):

$$K_{i,\,app} = \text{IC}_{50}/(1 + ([\text{radioligand}]/K_d))$$

Compounds of Formula I were tested according to procedures described above. The results are set forth below in Table 1 according to the following key:

A=K$_i$<500 nM
B=K$_i$>500 nM and <1000 nM
C=K$_i$>1000 nM

| Ex. No. | Human 5-HT6 Ki app (nM) |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | C |
| 22 | A |
| 23 | A |
| 24 | A |
| 25 | A |
| 26 | C |
| 27 | A |
| 28 | A |
| 29 | A |
| 30 | A |
| 31 | A |
| 32 | C |
| 33 | A |
| 34 | A |
| 35 | C |
| 36 | A |
| 37 | A |
| 38 | A |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | A |
| 51 | A |
| 52 | B |
| 53 | A |
| 54 | A |
| 55 | A |
| 56 | A |
| 57 | B |
| 58 | C |
| 59 | B |
| 60 | C |
| 61 | A |
| 62 | C |
| 63 | A |
| 64 | C |
| 65 | B |
| 66 | C |
| 67 | A |
| 68 | A |
| 69 | C |
| 70 | A |
| 71 | C |
| 72 | C |
| 73 | B |
| 74 | C |
| 75 | C |
| 76 | A |
| 77 | C |
| 78 | C |
| 79 | C |

-continued

| Ex. No. | Human 5-HT6 Ki app (nM) |
|---|---|
| 80 | C |
| 81 | C |
| 82 | C |
| 83 | C |
| 84 | C |
| 85 | C |
| 86 | C |
| 87 | C |
| 88 | A |
| 89 | A |
| 90 | A |
| 91 | A |
| 92 | A |
| 93 | A |
| 94 | A |
| 95 | A |
| 96 | A |
| 97 | A |
| 98 | C |
| 99 | C |
| 100 | A |
| 101 | C |
| 102 | C |
| 103 | C |
| 104 | A |
| 105 | A |
| 106 | A |
| 107 | A |
| 108 | A |
| 109 | A |
| 110 | A |
| 111 | A |

Actual data from a selection of compounds is provided below:

| Ex. No. | Human 5-HT$_6$ K$_i$ (nM) |
|---|---|
| 22 | 51.5 |
| 57 | 503.8 |
| 97 | 221.1 |
| 104 | 2.5 |
| 110 | 98.4 |

EXAMPLES

The following non-limiting Examples and Preparations illustrate the preparation of compounds of the present application. Proton ($^1$H) Nuclear magnetic resonance (NMR) spectra were in all cases consistent with the proposed structures. Characteristic chemical shifts (δ) are given in parts-per-million downfield from tetramethylsilane using conventional abbreviations for designation of major peaks: e.g., s, singlet; d, doublet; t, triplet; q, quartet; m, multiplet; br, broad. The mass spectra (m/z) were recorded using either electrospray ionisation (ESI) or atmospheric pressure chemical ionisation (APCI). The following abbreviations have been used for common solvents, reagents or reaction conditions: CDCl$_3$, deuterochloroform; D$_6$-DMSO, deuterodimethylsulphoxide; CD$_3$OD, deuteromethanol; THF, tetrahydrofuran; DCM, dichloromethane; TFA, trifluoroacetic acid, MeCN, AcCN, or ACN, acetonitrile; DMF, N,N-dimethylformamide; DMSO, dimethylsulfoxide; MeOH, methanol; mCPBA, meta-chloroperbenzoic acid; HCl, hydrochloric acid; DIEA, N,N-diethylisopropyl amine; DBU, (1,8-diazabicyclo[5.4.0] undec-7-ene); EtOAc, ethyl acetate; rt, RT or r.t., room temperature; h.v., house vacuum; dec., decomposition; SFC, supercritical fluid chromatography. Where thin layer chromatography (TLC) has been used it refers to silica gel TLC using silica gel 60 F$_{254}$ plates, R$_f$ is the distance travelled by a compound divided by the distance travelled by the solvent front on a TLC plate.

Preparative LC-MS

Various compounds described below were purified using preparative LC-MS. Unless otherwise described, the compounds were purified using a WATERS Fractionlynx system equipped with a YMC Pack Pro C$_{18}$ Column (5 μm, 120 Å, 50×20 mm) and the following solvent system: H$_2$O, AcCN, and 2% TFA in H$_2$O. Specific elution gradients were based on the retention times obtained with an analytical LC-MS, however, in general all elution gradients of H$_2$O and MeCN were run over a 7 minute run time with a flow rate of 35 mL/min. An autoblend method was used to ensure a concentration of 0.1% TFA throughout each run.

Alternatively, the compounds were purified using a WATERS Fractionlynx system equipped with a XBridge Prep C$_{18}$ OBD Column (5 μm, 30×75 mm) using the solvent system and autoblend method described above. Specific elution gradients were based on the retention times obtained with an analytical LC-MS, however, in general all elution gradients of H$_2$O and MeCN were run over a 8 minute run time with a flow rate of 50 mL/min.

Analytical LC-MS

Analytical LC-MS was performed on a WATERS Acquity UPLC-MS instrument equipped with a ACQUITY UPLC BEH C$_{18}$ Column (2.1×50 mm, 1.7 μm), a column temperature of 45° C. and using the following solvent system: Solvent A: 0.1% HCOOH in H$_2$O; and Solvent B: 0.1% HCOOH in AcCN. All compounds were run using the same elution gradient, i.e., 5% to 95% Solvent B over a 1.5 min run time with a flow rate of 0.6 mL/min.

Preparative Chiral SFC Separation

Stereoisomer mixtures were separated using a Berger Minigram SFC instrument on one of the following columns: ChiralPak AS-H (10×250 mm), ChiralPak IA (10×250 mm), ChiralPak AD-H (21×250 mm), Phenomenex Lux-2 (21.2× 250 mm), or ChiralPak IC (10×250 mm); eluting with either 0.1% diethylamine in MeOH/CO$_2$, or 0.1% diethylamine in EtOH/CO$_2$ or 0.1% diethylamine in isopropanol/CO$_2$ with a flow rate of 2.5 mL/min and a column temperature of 35° C.

Analytical Chiral SFC Separation

Stereoisomer mixtures or single enantiomers were analyzed using a JASCO analytical SFC instrument on one of the following columns: ChiralPak AS-H (4.6×250 mm), ChiralPak IA (4.6×250 mm), ChiralPak AD-H (4.6×250 mm), Phenomenex Lux-2 (4.6×250 mm), or ChiralPak IC (4.6×250 mm); eluting with either 0.1% diethylamine in MeOH/CO$_2$, or 0.1% diethylamine in EtOH/CO$_2$ or 0.1% diethylamine in isopropanol/CO$_2$, with a flow rate of 6.0 mL/min and a column temperature of 35° C.

It should be understood that for compounds exemplified here, the configuration at the ring juncture is cis. For examples where a racemic mixture is subjected to chiral separation, the absolute stereochemistry of the isolated compounds was not determined.

P01

Tert-butyl 7-iodo-1,3a,4,9b-tetrahydrochromeno[3,4-b]pyrrole-3(2H)-carboxylate

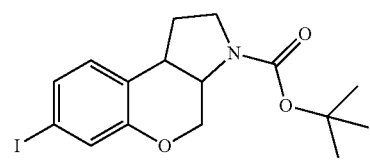 [SMILES: CC(C)(C)OC(=O)N1CCC2c3ccc(I)cc3OCC21]

Step 1

Tert-butyl 2-[(2-bromo-5-methoxyphenoxy)methyl]-2,5-dihydro-1H-pyrrole-1-carboxylate

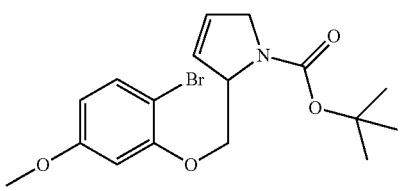 [SMILES: COc1ccc(Br)c(OCC2C=CCN2C(=O)OC(C)(C)C)c1]

To a solution of tert-butyl 2-(hydroxymethyl)-2,5-dihydro-1H-pyrrole-1-carboxylate (8.96 g, 0.45 mol, from Specialty Chemicals, Inc.) and 2-bromo-5-methoxyphenol (9.32 g, 0.46 mol) in THF (180 mL) was added DEAD (20.5 mL) in toluene (40 wt %) dropwise at 0° C. The reaction was stirred for 21 h at RT and the solvent was evaporated. The residue was suspended in methyl tert-butylether (50 mL) and the solution was filtered and concentrated. The resulting residue was dissolved in DCM, washed with 0.6N NaOH (2×25 mL) and the layers were separated. The organic layer was dried with Na$_2$SO$_4$ and the solvent was evaporated. The crude product was purified using an ISCO instrument (330 g RediSep® column), eluting with a gradient of ethyl acetate in heptane (from 0%-20% ethyl acetate over 6 minutes, then 29% ethyl acetate for 20 min) to afford 16.4 g of the title product.

Step 2

Tert-butyl 7-methoxy-1,3a,4,9b-tetrahydrochromeno[3,4-b]pyrrole-3(2H)-carboxylate

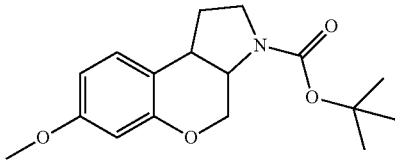 [SMILES: COc1ccc2c(c1)OCC1C2CCN1C(=O)OC(C)(C)C]

Tert-butyl 2-[(2-bromo-5-methoxyphenoxy)methyl]-2,5-dihydro-1H-pyrrole-1-carboxylate (16.4 g, 0.43 mol) was dissolved in toluene (790 mL) and heated at 50° C. for 20 min. To this solution was added AIBN (781 mg, 0.047 mol) and tributyltin hydride (17.9 mL, 0.67 mol). The reaction mixture was stirred at 80° C. for 16 h, cooled to RT, and DBU (10.7 g, 0.70 mol) was added. The resulting suspension was filtered through a pad of silica gel (100 g), and the solids washed with methyl tert-butylether. The filtrate was evaporated and the resulting oil triturated with heptane (10 mL). The crude product was collected via filtration and purified using an ISCO instrument (330 g RediSep® column), eluting with a gradient of ethyl acetate in heptane (from 5%-20%) to afford the title product. MS m/z 249 [M−tBu+H]$^+$

Step 3

Tert-butyl 7-hydroxy-1,3a,4,9b-tetrahydrochromeno[3,4-b]pyrrole-3(2H)-carboxylate

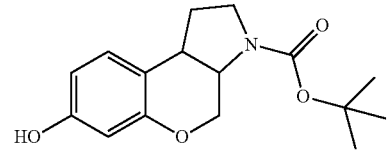 [SMILES: CC(C)(C)OC(=O)N1CCC2c3ccc(O)cc3OCC21]

A solution of boron tribromide (88 mL, 1 M, 88 mmol) in DCM was added to a solution of tert-butyl 7-methoxy-1,3a,4,9b-tetrahydrochromeno[3,4-b]pyrrole-3(2H)-carboxylate (8.6 g, 29 mmol) in DCM (204 mL) over 30 min at −78° C. The reaction mixture was kept at −78° C. for 30 min and then stirred at 0° C. for 30 min. Water (29 mL) and an aqueous solution of NaOH (95 mL, 3 M) were then added, followed by di-tert-butyl dicarbonate (11.4 g, 52.3 mmol). After stirring for 3 h, the layers were separated. The organic layer was washed with 0.1 N HCl, H$_2$O, and the solvent was removed. The resulting residue was triturated using heptane. The crude product was recovered via filtration and was used in the next reaction step without further purification. MS m/z 235 [M−tBu+H]$^+$

Step 4

Tert-butyl 7-iodo-1,3a,4,9b-tetrahydrochromeno[3,4-b]pyrrole-3(2H)-carboxylate

A solution of triflic anhydride (3.94 g, 23 mmol) was added dropwise to a solution of tert-butyl 7-hydroxy-1,3a,4,9b-tetrahydrochromeno[3,4-b]pyrrole-3(2H)-carboxylate (6.82 g, 23.4 mol) and triethylamine (46.9 g) in DCM (234 mL) at −78° C. After stirring for 1 h, H$_2$O (150 mL) was added and the layers were separated. The organic layer was washed with brine, dried over Na$_2$SO$_4$, filtered and concentrated to provide the crude product which was used without further purification. To a solution of tert-butyl 7-{[(trifluoromethyl)sulfonyl]oxy}-1,3a,4,9b-tetrahydrochromeno[3,4-b]pyrrole-3(2H)-carboxylate (8.46 g, 20 mmol), [1,1'-bis(diphenyl-phosphino)ferrocene]dichloropalladium II in DCM (571 mg, 0.7 mmol) and [1,1'-bis(diphenyl-phosphino)ferrocene](388 mg, 0.7 mmol) in DCE (200 mL), was added diisopropylethylamine (10.4 mL, 60 mmol) followed by pinacolborane (8.8 mL, 60 mmol). The reaction mixture was heated at 80° C. for 2 h and the solvent was evaporated. The crude product was partially purified using an ISCO instrument (120 g RediSep® column), eluting with a gradient of ethyl acetate in heptane (20% ethyl acetate for 3 min, from 20% to 30% ethyl acetate for 4 min, 30% ethyl acetate for 10 min). The fractions containing the product were collected and the solvent evaporated. The resulting residue was dissolved in DCM and the solution was concentrated to precipitate the pinacoloboronate product, which was collected via filtration.

Tert-butyl 7-(4,4,5,5-tetramethyl-1,3,2-dioxaborolan-2-yl)-1,3a,4,9b-tetrahydrochromeno[3,4-b]pyrrole-3(2H)-carboxylate (6.15 g, 15 mmol) was dissolved in THF (150 mL) and a solution of chloramine T (12.6 g, 45 mmol) in MeOH (90 mL) was added. A solution of sodium iodide (6.75 g, 45 mmol) in H$_2$O (90 mL) was then added over 20 min. The reaction mixture was stirred for 24 hours and the solvent was evaporated. The crude product was purified using an ISCO instrument (120 g RediSep® column), eluting with 30% ethyl acetate in heptane. The fractions containing the product were collected and the solvent evaporated. The resulting reside was dissolved in acetonitrile to precipitate the title compound. MS m/z 424 [M+Na]⁺.

Separation of the racemic mixture of tert-butyl 7-iodo-1,3a,4,9b-tetrahydrochromeno[3,4-b]pyrrole-3(2H)-carboxylate P01 was performed using a Berger Minigram SFC instrument on a Chiralpak IA column (3×15 cm), eluting with 50% MeOH: 0.1% diethylamine and $CO_2$ at 100 bar, using a flow rate of 100 mL/min. Each enantiomer was obtained as a free base and was subsequently converted to the hydrochloric acid salt by dissolving the product in DCM, adding 1M HCl in $Et_2O$ and evaporating the solvent.

Tert-butyl 7-iodo-3,4,4a,9a-tetrahydro[1]benzofuro[2,3-c]pyridine-2(1H)-carboxylate, enantiomer 1 P02. MS m/z 424 [M+Na]⁺.

Tert-butyl 7-iodo-3,4,4a,9a-tetrahydro[1]benzofuro[2,3-c]pyridine-2(1H)-carboxylate, enantiomer 1 P03. MS m/z 424 [M+Na]⁺.

P04

Tert-butyl 8-iodo-1,3a,4,9b-tetrahydrochromeno[3,4-b]pyrrole-3(2H)-carboxylate

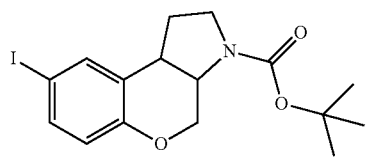 [SMILES: CC(C)(C)OC(=O)N1CCC2c3cc(I)ccc3OCC21]

Step 1

Tert-butyl 2-[(2-bromo-phenoxy)methyl]-2,5-dihydro-1H-pyrrole-1-carboxylate

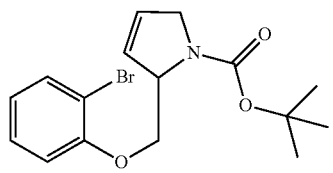 [SMILES: CC(C)(C)OC(=O)N1CC=CC1COc1ccccc1Br]

A solution of DEAD (25.1 mL) in toluene (40 wt %) was added dropwise to a solution of tert-butyl 2-(hydroxymethyl)-2,5-dihydro-1H-pyrrole-1-carboxylate (10 g, 0.56 mol) and 2-bromo-5-methoxyphenol (10.9 g, 0.55 mol) in THF (219 mL) at 0° C. After the addition, the reaction was stirred for 18 h at RT and the solvent was evaporated. The resulting residue was suspended in methyl tert-butylether (50 mL) and filtered. The combined filtrate was washed with 0.6 N NaOH (2×25 mL). The organic layer was dried with $Na_2SO_4$ and the solvent was evaporated. The resulting residue was purified using an ISCO instrument (330 g RediSep® column), eluting with a gradient of ethyl acetate in heptane (from 10% ethyl acetate for 10 minutes, then 20% ethyl acetate for 20 min) to provide 14.2 g of the bromo ether.

Step 2

Tert-butyl 1,3a,4,9b-tetrahydrochromeno[3,4-b]pyrrole-3(2H)-carboxylate

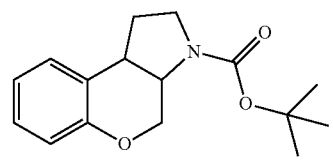 [SMILES: CC(C)(C)OC(=O)N1CCC2c3ccccc3OCC21]

Tert-butyl 2-[(2-bromo-phenoxy)methyl]-2,5-dihydro-1H-pyrrole-1-carboxylate (14.2 g, 0.38 mol) was dissolved in toluene (707 mL) and heated at 50° C. for 20 min. To this solution was added AIBN (688 mg, 0.049 mol) and tributyltin hydride (16 mL, 0.61 mol) at room temperature. The reaction mixture was stirred at 80° C. for 16 h and then DBU (9.5 mL, 0.62 mol) was added. The resulting suspension was filtered through a pad of silica gel (100 g) and the solids washed with methyl tert-butylether. The filtrate was evaporated. The crude product was purified using an ISCO instrument (330 g RediSep® column), eluting with a gradient of ethyl acetate in heptane (from 10% ethyl acetate in 10 minutes, then 20% ethyl acetate for 15 min) to provide the title product. MS m/z 299 [M+Na]⁺

Step 3

Tert-butyl 8-iodo-1,3a,4,9b-tetrahydrochromeno[3,4-b]pyrrole-3(2H)-carboxylate P04

Zinc chloride (2.49 g, 18.3 mmol) and benzyltrimethylammonium dichloroiodate (4.25 g, 12.2 mmol) were added to a suspension of tert-butyl 1,3a,4,9b-tetrahydrochromeno[3,4-b]pyrrole-3(2H)-carboxylate (2.8 g, 10.2 mmol) in acetic acid (30 mL). The reaction mixture was stirred at 50° C. for 16 h, cooled to r.t. and DCM (60 mL) was added followed by $H_2O$ (60 mL). The layers were separated. The organic layer was washed with $H_2O$ (2×) and saturated $NaHSO_3$ (15 mL), and the solvent was evaporated to afford 8-iodo-1,3a,4,9b-tetrahydrochromeno[3,4-b]pyrrole, which was taken directly in the next step.

To a solution of 8-iodo-1,3a,4,9b-tetrahydrochromeno[3,4-b]pyrrole (750 mg, 2.5 mmol) in DCM (20 mL), was added di-tert-butyldicarbonate (858 µL, 3.74 mmol). The reaction mixture was stirred for 30 min and the solvent was evaporated. The residue was purified on silica gel using an ISCO instrument (330 g RediSep® column) and eluting with a gradient of ethyl acetate in hexanes (from 0% ethyl acetate to 20% ethyl acetate over 20 min) to afford the title product P04. MS m/z 424 [M+Na]⁺

Separation of racemic tert-butyl 8-iodo-1,3a,4,9b-tetrahydrochromeno[3,4-b]pyrrole-3(2H)-carboxylate P04 was performed using a Berger Minigram SFC instrument on a Phenomenex Lux-2 column (21.2×250 cm), eluting with 20% MeOH: 0.1% diethylamine and $CO_2$, at 100 bar, using a flow rate of 52 mL/min. Each enantiomer was obtained as a free base and subsequently converted to the hydrochloric acid salt by dissolving the product in DCM, adding 1M HCl in $Et_2O$ and evaporating the solvent.

Tert-butyl 8-iodo-3,4,4a,9a-tetrahydro[1]benzofuro[2,3-c]pyridine-2(1H)-carboxylate, enantiomer 1 P05. MS m/z 424 [M+Na]⁺.

Tert-butyl 8-iodo-3,4,4a,9a-tetrahydro[1]benzofuro[2,3-c]pyridine-2(1H)-carboxylate, enantiomer 2 P06. MS m/z 424 [M+Na]⁺.

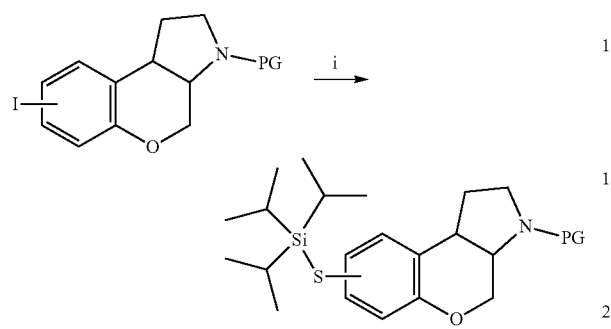

i. (Ph₃P)₄Pd, TIPSi—SH, LHMDS, dioxane

P07

Tert-butyl 7-[(tripropan-2-ylsilyl)sulfanyl]-1,3a,4,9b-tetrahydrochromeno[3,4-b]pyrrole-3(2H)-carboxylate (Enantiomer 1)

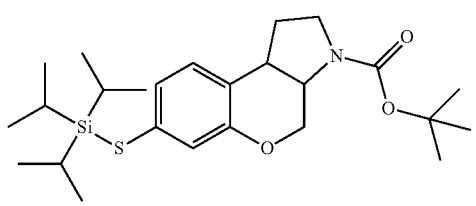 [SMILES: CC(C)[Si](Sc1ccc2c(c1)OCC1C2CCN1C(=O)OC(C)(C)C)(C(C)C)C(C)C]

Anhydrous dioxane was sparged with argon gas for 1 h before being used. Triisopropylsilanethiol (0.95 mL, 4.4 mmol) was dissolved into anhydrous 1,4-dioxane (3 mL) and to this 1.0 M lithium hexamethyldisilazide in THF (4.2 mL, 4.2 mmol) was added slowly. The reaction was stirred for 2.5 h. A portion of the lithium triisopropylsilanethiolate solution (2.64, 1.32 mmol) was added to a suspension of tert-butyl 7-iodo-1,3a,4,9b-tetrahydrochromeno[3,4-b]pyrrole-3(2H)-carboxylate P02 (480 mg, 1.2 mmol) and tetrakis(triphenylphosphine)palladium(0) (139 mg, 0.12 mmol) in 1,4-dioxane (2 mL) under argon. The reaction mixture was stirred at 60° C. for 16 h and the solvent was evaporated. The residue was triturated with anhydrous hexane, filtered through a plug of celite, and the filtrate concentrated to yield the crude product which was used in the next step without further purification. MS m/z 408 [M−tBu+H]⁺.

P08

Tert-butyl 7-[(tripropan-2-ylsilyl)sulfanyl]-1,3a,4,9b-tetrahydrochromeno[3,4-b]pyrrole-3(2H)-carboxylate (Enantiomer 2)

Prepared as described for Enantiomer 1 of tert-butyl 7-[(tripropan-2-ylsilyl)sulfanyl]-1,3a,4,9b-tetrahydrochromeno[3,4-b]pyrrole-3(2H)-carboxylate P07 starting from enantiomer 2 of tert-butyl 7-iodo-1,3a,4,9b-tetrahydrochromeno[3,4-b]pyrrole-3(2H)-carboxylate P03. MS m/z 408 [M−tBu+H]⁺.

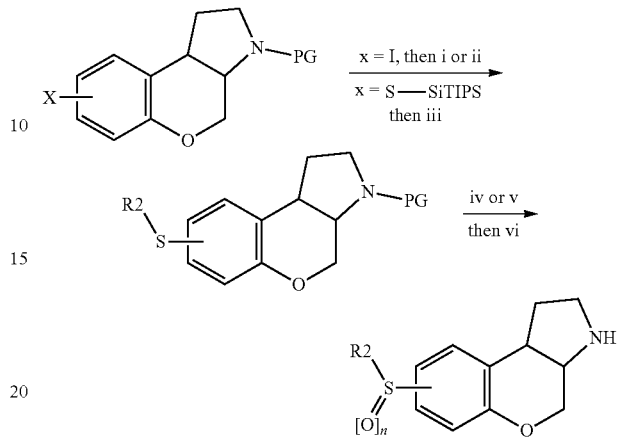

i. R2-SH, CuI, neocuproine, DMF, 90° C. ii. R2-S-SiTIPS, CuI, CsF, 90° C., DMF. iii. R2-I, CuI, CsF, 90° C., DMF. iv. mCPBA, DCM. v. Benzenesulfonylphenyloxaziridine, DCM. vi. TFA: DCM (1:1).

Example 1

7-[(3-Fluorophenyl)sulfonyl]-1,2,3,3a,4,9b-hexahydrochromeno[3,4-b]pyrrole (Enantiomer 1)

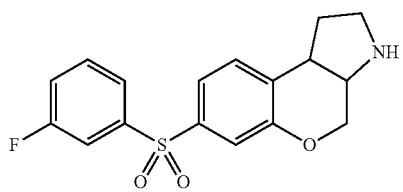 [SMILES: O=S(=O)(c1cccc(F)c1)c1ccc2c(c1)OCC1NCCC21]

Step 1

Tert-butyl 7-(3-fluorophenylsulfanyl)-1,2,3,3a,4,9b-hexahydrochromeno[3,4-b]pyrrole-3(2H)-carboxylate

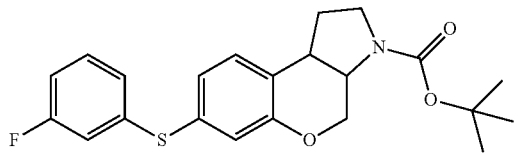 [SMILES: CC(C)(C)OC(=O)N1CCC2c3ccc(Sc4cccc(F)c4)cc3OCC21]

Anhydrous DMF was sparged with argon gas for 1 h before being used. A reaction vial was charged with 375 µL of a 0.625 M stock solution of tert-butyl 7-iodo-1,3a,4,9b-tetrahydrochromeno[3,4-b]pyrrole-3(2H)-carboxylate P02 (60 mg, 0.150 mmol) in DMF, 150 µL of a 0.10 M stock solution of neocuproine (3.1 mg, 0.015 mmol) in DMF, and 290 µL of a 0.31 M stock solution of copper(I) iodide (17 mg, 0.09 mmol) in DMF. To this was added 3-fluoro-benzenethiol (42 µL, 0.33 mmol, 2.2 eq) neat followed by 315 μL of a 1.0 M stock solution of sodium tert-butoxide (30.2 mg, 0.315 mmol) in DMF. The reaction mixture was shaken at 100° C. for 16 h and the solvent was evaporated. The residue was suspended into DCE:MeOH 95:5 (2.0 mL), passed through a silica gel column (1 g), eluting with DCE:MeOH 95:5 (3×2.0 mL). The eluent was concentrated to yield crude tert-butyl 7-(3-fluorophenylsulfanyl)-1,2,3,3a,4,9b-hexahydrochromeno[3,4-b]pyrrole-3(2H)-carboxylate which was used in the next step without further purification.

Step 2

7-[(3-Fluorophenyl)sulfonyl]-1,2,3,3a,4,9b-hexahydrochromeno[3,4-b]pyrrole Enantiomer 1

Tert-butyl 7-(3-fluorophenylsulfanyl)-1,2,3,3a,4,9b-hexahydrochromeno[3,4-b]pyrrole-3(2H)-carboxylate (0.15 mmol, 1.0 eq) was suspended in DCE (1 mL) and to this a solution of 0.5 M of m-CPBA (70% from ACROS) in DCE (1.2 mL, 0.6 mmol, 4.0 eq) was added slowly. The reaction mixture was shaken for 10 min and diluted with DCE (2.0 mL) and 1N aqueous NaOH (2 mL) was added. The mixture was shaken, centrifuged and the aqueous layer was removed. The organic solution was then washed with 1N aqueous NaOH (2 mL) twice and $H_2O$ (2 mL) once. The organic layer was transferred into a new glass tube and the solvent was evaporated. The resulting oil was dissolved in a 1:1 mixture of TFA:DCM. (2.0 mL). The solution was shaken for 30 min and the solvent was evaporated. The crude product was purified by preparative LC/MS and concentrated to afford the product as a trifluoroacetic acid salt. The product was then dissolved into a small amount of DCM, treated with 1.0 N HCl in diethyl ether, and the solvent evaporated to afford 7-(3,5-difluoro-benzenesulfonyl)-1,2,3,4-tetrahydro-benzo[4,5]furo[2,3-c]pyridine hydrochloride. MS m/z 334 [M+H]$^+$. $^1$H-NMR (400 MHz, DMSO-$d_6$): $^1$H-NMR (400 MHz, DMSO-$d_6$): δ 1.92-1.97 (m, 1H), 2.51-2.54 (m, 1H), 2.98 (bs, 1H), 3.20 (bs, 1H), 3.72 (q, J=1.4 Hz, 1H), 4.1 (bs, 1H), 4.24-4.32 (m, 2H), 7.49 (s, 1H), 7.55-7.71 (m, 4H), 7.83 (d, J=1.9 Hz, 1H), 7.87 (d, J=1.9 Hz, 1H), 9.08 (bs, 1H), 9.78 (bs, 1H).

The following examples were prepared essentially as described above. All compounds were isolated as the HCl salt.

Examples 21, 22 and 23 were obtained from the same reaction mixture after LC-MS purification.

| Ex No. | Chemical Name | MS m/z [M + H]$^+$ | Stereochemistry | Scaffold | Starting material |
|---|---|---|---|---|---|
| 1 | 7-[(3-fluorophenyl)sulfonyl]-1,2,3,3a,4,9b-hexahydrochromeno[3,4-b]pyrrole | 334.1 | Enantiomer 1 | P02 | 3-fluorobenzenethiol |
| 2 | 7-[(3-chlorophenyl)sulfonyl]-1,2,3,3a,4,9b-hexahydrochromeno[3,4-b]pyrrole | 350.1 | Enantiomer 1 | P02 | 3-chlorobenzenethiol |
| 3 | 7-[(3,5-dichlorophenyl)sulfonyl]-1,2,3,3a,4,9b-hexahydrochromeno[3,4-b]pyrrole | 384.0 | Enantiomer 1 | P02 | 3,5-dichlorobenzenethiol |
| 4 | 7-[(4-fluorophenyl)sulfonyl]-1,2,3,3a,4,9b-hexahydrochromeno[3,4-b]pyrrole | 334.1 | Enantiomer 1 | P02 | 4-fluorobenzenethiol |
| 5 | 7-[(3,5-difluorophenyl)sulfonyl]-1,2,3,3a,4,9b-hexahydrochromeno[3,4-b]pyrrole | 352.1 | Enantiomer 1 | P02 | 3,5-difluorobenzenethiol |
| 6 | 7-[(3-chloro-5-fluorophenyl)sulfonyl]-1,2,3,3a,4,9b-hexahydrochromeno[3,4-b]pyrrole | 368.0 | Enantiomer 1 | P02 | 3-chloro-5-fluorobenzenethiol |
| 7 | 7-{[3-(trifluoromethoxy)phenyl]sulfonyl}-1,2,3,3a,4,9b-hexahydrochromeno[3,4-b]pyrrole | 400.1 | Enantiomer 1 | P02 | 3-(trifluoromethoxy)benzenethiol |
| 8 | 7-{[3-(trifluoromethyl)phenyl]sulfonyl}-1,2,3,3a,4,9b-hexahydrochromeno[3,4-b]pyrrole | 384.1 | Enantiomer 1 | P02 | 3-(trifluoromethyl)benzenethiol |
| 9 | 7-{[3-(propan-2-yloxy)phenyl]sulfonyl}-1,2,3,3a,4,9b-hexahydrochromeno[3,4-b]pyrrole | 374.1 | Enantiomer 1 | P02 | 3-(propan-2-yloxy)benzenethiol |
| 10 | 7-[(3-fluorophenyl)sulfonyl]- | 334.1 | Enantiomer 2 | P03 | 3-fluorobenzenethiol |

| Ex No. | Chemical Name | MS m/z [M + H]+ | Stereochemistry | Scaffold | Starting material |
|---|---|---|---|---|---|
| | 1,2,3,3a,4,9b-hexahydrochromeno[3,4-b]pyrrole | | | | |
| 11 | 7-[(3-chlorophenyl)sulfonyl]-1,2,3,3a,4,9b-hexahydrochromeno[3,4-b]pyrrole | 350.1 | Enantiomer 2 | P03 | 3-chlorobenzenethiol |
| 12 | 7-[(3,5-dichlorophenyl)sulfonyl]-1,2,3,3a,4,9b-hexahydrochromeno[3,4-b]pyrrole | 384.0 | Enantiomer 2 | P03 | 3,5-dichlorobenzenethiol |
| 13 | 7-[(4-fluorophenyl)sulfonyl]-1,2,3,3a,4,9b-hexahydrochromeno[3,4-b]pyrrole | 334.1 | Enantiomer 2 | P03 | 4-fluorobenzenethiol |
| 14 | 7-[(3,5-difluorophenyl)sulfonyl]-1,2,3,3a,4,9b-hexahydrochromeno[3,4-b]pyrrole | 352.1 | Enantiomer 2 | P03 | 3,5-difluorobenzenethiol |
| 15 | 7-[(3-chloro-5-fluorophenyl)sulfonyl]-1,2,3,3a,4,9b-hexahydrochromeno[3,4-b]pyrrole | 368.0 | Enantiomer 2 | P03 | 3-chloro-5-fluorobenzenethiol |
| 16 | 7-{[3-(trifluoromethoxy)phenyl]sulfonyl}-1,2,3,3a,4,9b-hexahydrochromeno[3,4-b]pyrrole | 400.1 | Enantiomer 2 | P03 | 3-(trifluoromethoxy)benzenethiol |
| 17 | 7-{[3-(trifluoromethyl)phenyl]sulfonyl}-1,2,3,3a,4,9b-hexahydrochromeno[3,4-b]pyrrole | 384.1 | Enantiomer 2 | P03 | 3-(trifluoromethyl)benzenethiol |
| 18 | 7-{[3-(propan-2-yloxy)phenyl]sulfonyl}-1,2,3,3a,4,9b-hexahydrochromeno[3,4-b]pyrrole | 374.1 | Enantiomer 2 | P03 | 3-(propan-2-yloxy)benzenethiol |
| 19 | 7-(naphthalen-1-ylsulfonyl)-1,2,3,3a,4,9b-hexahydrochromeno[3,4-b]pyrrole | 366.1 | Enantiomer 1 | P02 | naphthalene-1-thiol |
| 20 | 7-(naphthalen-1-ylsulfonyl)-1,2,3,3a,4,9b-hexahydrochromeno[3,4-b]pyrrole | 366.1 | Enantiomer 2 | P03 | naphthalene-1-thiol |
| 21 | 7-[(6-methylpyridin-2-yl)sulfanyl]-1,2,3,3a,4,9b-hexahydrochromeno[3,4-b]pyrrole | 299.1 | Enantiomer 1 | P02 | 6-methylpyridine-2-thiol |
| 22 | 7-[(6-methylpyridin-2-yl)sulfinyl]-1,2,3,3a,4,9b-hexahydrochromeno[3,4-b]pyrrole | 315.1 | Enantiomer 1 | P02 | 6-methylpyridine-2-thiol |
| 23 | 7-[(6-methylpyridin-2-yl)sulfonyl]-1,2,3,3a,4,9b-hexahydrochromeno[3,4-b]pyrrole | 331.1 | Enantiomer 1 | P02 | 6-methylpyridine-2-thiol |
| 24 | 7-[(6-methylpyridin-2-yl)sulfonyl]-1,2,3,3a,4,9b-hexahydrochromeno[3,4-b]pyrrole | 331.1 | Enantiomer 2 | P03 | 6-methylpyridine-2-thiol |

Example 25

7-(Phenylsulfinyl)-1,2,3,3a,4,9b-hexahydro-chromeno[3,4-b]pyrrole

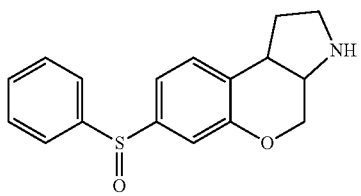 [SMILES: O=S(c1ccccc1)c1ccc2c(c1)OCC1NCCC21]

Tert-butyl 7-(phenylsulfanyl)-1,2,3,3a,4,9b-hexahydrochromeno[3,4-b]pyrrole-3(2H)-carboxylate was prepared as described for tert-butyl 7-(3-fluorophenylsulfanyl)-1,2,3,3a,4,9b-hexahydrochromeno[3,4-b]pyrrole-3(2H)-carboxylate (see Example 1) starting from tert-butyl 7-iodo-1,3a,4,9b-tetrahydrochromeno[3,4-b]pyrrole-3(2H)-carboxylate P02 and benzenethiol. Oxidation step (below) provided a racemic product.

The thioether (57.5 mg, 0.15 mmol) was dissolved in anhydrous DCM (1.0 mL). 2-Benzenesulfonyl-3-phenyl-oxaziridine (58.8 mg, 0.22 mmol) was added and the reaction was stirred at RT for 4.5 hours. The reaction solution was concentrated and the residue dissolved into DCM:TFA (1:1, 2.0 mL). The reaction was shaken for 15 minutes, concentrated and the crude product purified by preparative LC/MS. Conversion to the HCl salt was accomplished by dissolving the product in DCM, adding 1M HCl in Et$_2$O and evaporating the solvent. MS m/z 300.1 [M+H]$^+$. $^1$H-NMR (400 MHz, DMSO-d$_6$): δ 1.91 (bs, 1H), 2.51-2.54 (m, 1H), 2.96 (bs, 1H), 3.19 (bs, 1H), 3.63-3.68 (m, 1H), 4.07 (bs, 1H), 4.14-4.28 (m, 2H), 7.24 (s, 1H), 7.33-7.56 (m, 5H), 7.72-7.78 (m, 2H), 9.05 (bs, 1H), 9.74 (bs, 1H).

Example 26

7-(Phenylsulfinyl)-1,2,3,3a,4,9b-hexahydro-chromeno[3,4-b]pyrrole

Prepared as described for Example 25 starting from tert-butyl 7-iodo-1,3a,4,9b-tetrahydrochromeno[3,4-b]pyrrole-3 (2H)-carboxylate P03. Oxidation provided a racemic product.

MS m/z 300.1 [M+H]$^+$. $^1$H-NMR (400 MHz, DMSO-d$_6$): δ 1.91 (bs, 1H), 2.45-2.54 (m, 1H), 2.96 (bs, 1H), 3.19 (bs, 1H), 3.62-3.68 (m, 1H), 4.07 (bs, 1H), 4.19-4.28 (m, 2H), 7.24 (s, 1H), 7.33-7.56 (m, 5H), 7.72-7.78 (m, 2H), 9.05 (bs, 1H), 9.75 (bs, 1H).

Example 27

7-{[3-Fluoro-5-(propan-2-yloxy)phenyl]sulfonyl}-1,2,3,3a,4,9b-hexahydrochromeno[3,4-b]pyrrole (Enantiomer 1)

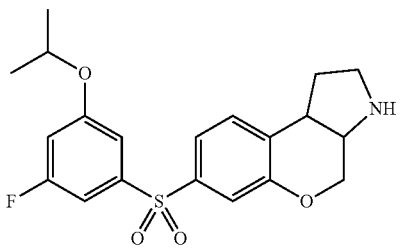 [SMILES: CC(C)Oc1cc(F)cc(S(=O)(=O)c2ccc3c(c2)OCC2NCCC32)c1]

Step 1

Tert-butyl 7-{[3-fluoro-5-(propan-2-yloxy)phenyl]sulfanyl}-1,2,3,3a,4,9b-hexahydrochromeno[3,4-b]pyrrole, Enantiomer 1

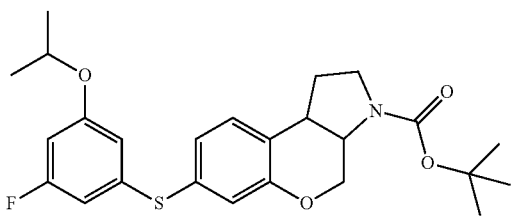 [SMILES: CC(C)Oc1cc(F)cc(Sc2ccc3c(c2)OCC2C3CCN2C(=O)OC(C)(C)C)c1]

Anhydrous DMF was sparged with argon gas for 1 h before being used. A one dram vial was charged with 3-fluoro-5-isopropoxy-iodobenzene (63 µL, 0.45 mmol, 1.5 eq), 300 µL (0.15 mmol) of a 0.5 M stock solution of tert-butyl 7-[(tripropan-2-ylsilyl)sulfanyl]-1,3a,4,9b-tetrahydrochromeno[3,4-b]pyrrole-3(2H)-carboxylate P07 in DMF, 150 µL of a 0.10 M stock solution of neocuproine (3.12 mg, 0.015 mmol) in DMF and 175 µL of a 0.30 M stock solution of copper (I) iodide (10 mg, 0.05 mmol). Solid cesium fluoride (25 mg, 0.16 mmol) was added and the reaction mixture shaken at 90° C. for 16 h. The solvent was evaporated and the residue suspended into DCE:MeOH 95:5 (1.0 mL), passed through a silica gel column (1 g) eluting with DCE:MeOH 95:5 (3×2.0 mL). The eluent was concentrated to yield crude tert-butyl 7-{[3-fluoro-5-(propan-2-yloxy)phenyl]sulfanyl}-1,2,3,3a,4,9b-hexahydrochromeno[3,4-b]pyrrole, Enantiomer 1, which was taken on without further purification.

Step 2

7-{[3-Fluoro-5-(propan-2-yloxy)phenyl]sulfonyl}-1,2,3,3a,4,9b-hexahydrochromeno[3,4-b]pyrrole, Enantiomer 1

Prepared as described for 7-[(3-fluorophenyl)sulfonyl]-1,2,3,3a,4,9b-hexahydrochromeno[3,4-b]pyrrole (Example 1, Step 2) starting from tert-butyl 7-{[3-fluoro-5-(propan-2-yloxy)phenyl]sulfanyl}-1,2,3,3a,4,9b-hexahydrochromeno[3,4-b]pyrrole, Enantiomer 1. MS m/z 392.1 [M+H]⁺. ¹H-NMR (400 MHz, DMSO-$d_6$): δ 1.26 (d, J=2.0 Hz, 1H), 1.91-2.0 (m, 1H), 2.51-2.54 (m, 1H), 2.99 (bs, 1H), 3.16-3.23 (m, 1H), 4.10 (bs, 1H), 4.26-4.32 (m, 2H), 4.73-4.79 (m, 1H), 7.18 (d, J=3.0 Hz 1H), 7.30 (s, 1H), 7.37 (d, J=1.8 Hz 1H), 7.51-7.64 (m, 3H), 9.08 (bs, 1H), 9.76 (bs, 1H).

The following examples were prepared essentially as described above. All compounds were isolated as HCl salts.

| Ex. # | Chemical Name | MS m/z [M + H]⁺ | Stereochemistry | Scaffold | Starting material |
|---|---|---|---|---|---|
| 27 | 7-{[3-fluoro-5-(propan-2-yloxy)phenyl]sulfonyl}-1,2,3,3a,4,9b-hexahydrochromeno[3,4-b]pyrrole | 392.1 | Enantiomer 1 | P07 | 1-fluoro-3-iodo-5-(propan-2-yloxy)benzene |
| 28 | 7-[(5-bromopyridin-3-yl)sulfonyl]-1,2,3,3a,4,9b-hexahydrochromeno[3,4-b]pyrrole | 395.0 | Enantiomer 1 | P07 | 3-bromo-5-iodopyridine |
| 29 | 7-[(5-fluoropyridin-3-yl)sulfonyl]-1,2,3,3a,4,9b-hexahydrochromeno[3,4-b]pyrrole | 335.1 | Enantiomer 1 | P07 | 3-fluoro-5-iodopyridine |
| 30 | 7-[(5-chloropyridin-3-yl)sulfonyl]-1,2,3,3a,4,9b-hexahydrochromeno[3,4-b]pyrrole | 351.0 | Enantiomer 1 | P07 | 3-chloro-5-iodopyridine |
| 31 | 7-[(5-bromopyridin-3-yl)sulfonyl]-1,2,3,3a,4,9b-hexahydrochromeno[3,4-b]pyrrole | 395.0 | Enantiomer 2 | P08 | 3-bromo-5-iodopyridine |
| 32 | 7-[(5-fluoropyridin-3-yl)sulfonyl]-1,2,3,3a,4,9b-hexahydrochromeno[3,4-b]pyrrole | 335.1 | Enantiomer 2 | P08 | 3-fluoro-5-iodopyridine |
| 33 | 7-[(5-methoxypyridin-3-yl)sulfonyl]-1,2,3,3a,4,9b-hexahydrochromeno[3,4-b]pyrrole | 347.1 | Enantiomer 1 | P07 | 3-iodo-5-methoxypyridine |
| 34 | 7-[(5-chloropyridin-3-yl)sulfonyl]-1,2,3,3a,4,9b-hexahydrochromeno[3,4-b]pyrrole | 351.0 | Enantiomer 2 | P08 | 3-chloro-5-iodopyridine |
| 35 | 7-[(5-methoxypyridin-3-yl)sulfonyl]-1,2,3,3a,4,9b-hexahydrochromeno[3,4-b]pyrrole | 347.1 | Enantiomer 2 | P08 | 3-iodo-5-methoxypyridine |
| 36 | 7-[(3-fluoro-5-methoxyphenyl)sulfonyl]-1,2,3,3a,4,9b-hexahydrochromeno[3,4-b]pyrrole | 364.1 | Enantiomer 1 | P07 | 1-fluoro-3-iodo-5-methoxybenzene |
| 37 | 7-(2,3-dihydro-1-benzofuran-4-ylsulfonyl)-1,2,3,3a,4,9b-hexahydrochromeno[3,4-b]pyrrole | 358.1 | Enantiomer 1 | P07 | 4-iodo-2,3-dihydro-1-benzofuran |
| 38 | 3-[(3aS,9bS)-1,2,3,3a,4,9b-hexahydrochromeno[3,4-b]pyrrol-7-ylsulfonyl]-N,N-dimethylbenzamide | 387.1 | Enantiomer 1 | P07 | 3-iodo-N,N-dimethylbenzamide |
| 39 | 7-{[3-fluoro-5-(2-methylpropoxy)phenyl]sulfonyl}-1,2,3,3a,4,9b-hexahydrochromeno[3,4-b]pyrrole | 406.1 | Enantiomer 1 | P07 | 1-fluoro-3-iodo-5-(2-methylpropoxy)benzene |
| 40 | 7-[(3-ethoxy-5-fluorophenyl)sulfonyl]-1,2,3,3a,4,9b- | 378.1 | Enantiomer 1 | P07 | 1-ethoxy-3-fluoro-5-iodobenzene |

-continued

| Ex. # | Chemical Name | MS m/z [M + H]+ | Stereochemistry | Scaffold | Starting material |
|---|---|---|---|---|---|
| | hexahydrochromeno[3,4-b]pyrrole | | | | |
| 41 | 7-[(2,3-difluorophenyl)sulfonyl]-1,2,3,3a,4,9b-hexahydrochromeno[3,4-b]pyrrole | 352.1 | Enantiomer 1 | P07 | 1,2-difluoro-3-iodobenzene |
| 42 | 7-[(2,3,5-trifluorophenyl)sulfonyl]-1,2,3,3a,4,9b-hexahydrochromeno[3,4-b]pyrrole | 370.1 | Enantiomer 1 | P07 | 1,2,5-trifluoro-3-iodobenzene |
| 43 | 7-{[3-fluoro-5-(propan-2-yloxy)phenyl]sulfonyl}-1,2,3,3a,4,9b-hexahydrochromeno[3,4-b]pyrrole | 392.1 | Enantiomer 2 | P08 | 1-fluoro-3-iodo-5-(propan-2-yloxy)benzene |
| 44 | 7-[(3-fluoro-5-methoxyphenyl)sulfonyl]-1,2,3,3a,4,9b-hexahydrochromeno[3,4-b]pyrrole | 364.1 | Enantiomer 2 | P08 | 1-fluoro-3-iodo-5-methoxybenzene |
| 45 | 7-(2,3-dihydro-1-benzofuran-4-ylsulfonyl)-1,2,3,3a,4,9b-hexahydrochromeno[3,4-b]pyrrole | 358.1 | Enantiomer 2 | P08 | 4-iodo-2,3-dihydro-1-benzofuran |
| 46 | 3-[(3aR,9bR)-1,2,3,3a,4,9b-hexahydrochromeno[3,4-b]pyrrol-7-ylsulfonyl]-N,N-dimethylbenzamide | 387.1 | Enantiomer 2 | P08 | 3-iodo-N,N-dimethylbenzamide |
| 47 | 7-{[3-fluoro-5-(2-methylpropoxy)phenyl]sulfonyl}-1,2,3,3a,4,9b-hexahydrochromeno[3,4-b]pyrrole | 406.1 | Enantiomer 2 | P08 | 1-fluoro-3-iodo-5-(2-methylpropoxy)benzene |
| 48 | 7-[(3-ethoxy-5-fluorophenyl)sulfonyl]-1,2,3,3a,4,9b-hexahydrochromeno[3,4-b]pyrrole | 378.1 | Enantiomer 2 | P08 | 1-ethoxy-3-fluoro-5-iodobenzene |
| 49 | 7-[(2,3-difluorophenyl)sulfonyl]-1,2,3,3a,4,9b-hexahydrochromeno[3,4-b]pyrrole | 352.1 | Enantiomer 2 | P08 | 1,2-difluoro-3-iodobenzene |
| 50 | 7-[(2,3,5-trifluorophenyl)sulfonyl]-1,2,3,3a,4,9b-hexahydrochromeno[3,4-b]pyrrole | 370.1 | Enantiomer 2 | P08 | 1,2,5-trifluoro-3-iodobenzene |
| 51 | 7-{[5-(trifluoromethyl)pyridin-3-yl]sulfonyl}-1,2,3,3a,4,9b-hexahydrochromeno[3,4-b]pyrrole | 385.1 | Enantiomer 1 | P02 | 3-(trifluoromethyl)-5-[(tripropan-2-ylsilyl)sulfanyl]pyridine |
| 52 | 7-{[5-(trifluoromethyl)pyridin-3-yl]sulfonyl}-1,2,3,3a,4,9b-hexahydrochromeno[3,4-b]pyrrole | 385.1 | Enantiomer 2 | P03 | 3-(trifluoromethyl)-5-[(tripropan-2-ylsilyl)sulfanyl]pyridine |

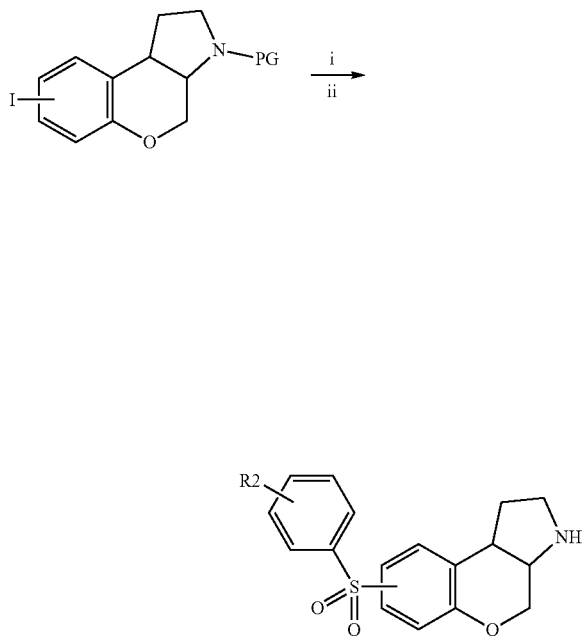

i. R2-SO2Na, CuI, N,N-dimethyl-1,2-ethandiamine, DIEA, DMSO, 90° C. ii. TFA: DCM (1:1)

Example 53

8-(Phenylsulfonyl)-1,2,3,3a,4,9b-hexahydrochromeno[3,4-b]pyrrole (Enantiomer 1)

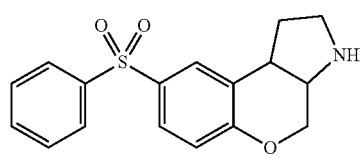 [SMILES: O=S(=O)(c1ccccc1)c1ccc2c(c1)C1CCNC1CO2]

Copper(I) iodide (19 mg, 0.10 mmol) was added to a stirring solution of N,N-dimethyl-1,2-ethanediamine (21 μL, 0.20 mmol) in DMSO (2 mL). The reaction was stirred at RT for 10 minutes. N,N-diisopropylethylamine (130 μL, 0.75 mmol), sodium benzenesulfinate (245 mg, 1.5 mmol) and tert-butyl-8-iodo-1,3a,4,9b-tetrahydrochromeno[3,4-b]pyrrole-3(2H)-carboxylate (P05, enantiomer 1,200 mg, 0.5 mmol) were then added sequentially. The reaction was stirred at 100° C. for 18 h. After cooling to RT, water (24 mL) was added and the resulting suspension was extracted with DCM (3×). The combined organic layers were washed with water (2×) and brine, dried over anhydrous sodium sulfate, filtered and concentrated. The resulting oil was stirred in TFA:DCM (1:1, 2 mL) for 30 min and the solvent was evaporated. This crude product was purified by preparative LC/MS. The resulting material was suspended in DCM, washed with 1N aqueous sodium hydroxide (3×) and water (3×) and the solvent evaporated. The product was converted to the HCl salt by dissolving the free base in a small amount of DCM, adding 1.0 N HCl in diethyl ether and evaporating the solvent to provide 132 mg of 8-(phenylsulfonyl)-1,2,3,3a,4,9b-hexahydrochromeno[3,4-b]pyrrole, Enantiomer 1. MS m/z 316 [M+H]$^+$. $^1$H-NMR (400 MHz, DMSO-d$_6$): δ 1.91-1.97 (m, 1H), 2.53-2.60 (m, 1H), 2.98-3.02 (m, 1H), 3.19-3.22 (m, 1H), 3.72-3.77 (m, 1H), 4.09 (bs, 1H), 4.24-4.32 (m, 2H), 7.09 (d, J=2.1 Hz, 1H), 7.59-7.74 (m, 4H), 7.94-7.99 (m, 3H), 9.13 (bs, 1H), 9.79 (bs, 1H).

The following examples were prepared essentially as described in the above synthetic steps. All compounds were isolated as HCl salts.

| Ex. No. | Chemical Name | MS m/z, [M + H]$^+$ | Stereochemistry | Scaffold | Starting material |
|---|---|---|---|---|---|
| 53 | 8-(phenylsulfonyl)-1,2,3,3a,4,9b-hexahydrochromeno[3,4-b]pyrrole | 316.1 | Enantiomer 1 | P02 | sodium benzenesulfinate |
| 54 | 8-(phenylsulfonyl)-1,2,3,3a,4,9b-hexahydrochromeno[3,4-b]pyrrole | 316.1 | Enantiomer 2 | P03 | sodium benzenesulfinate |
| 55 | 7-(phenylsulfonyl)-1,2,3,3a,4,9b-hexahydrochromeno[3,4-b]pyrrole | 316.1 | Enantiomer 1 | P05 | sodium benzenesulfinate |
| 56 | 7-(phenylsulfonyl)-1,2,3,3a,4,9b-hexahydrochromeno[3,4-b]pyrrole | 316.1 | Enantiomer 2 | P06 | sodium benzenesulfinate |

Example 54

$^1$H-NMR (400 MHz, DMSO-d$_6$): δ 1.89-1.97 (m, 1H), 2.53-2.60 (m, 1H), 2.96-3.02 (m, 1H), 3.18-3.24 (m, 1H), 3.75 (q, J=1.8 Hz 1H), 4.10 (bs, 1H), 4.25-4.32 (m, 2H), 7.09 (d, J=2.1 Hz, 1H), 7.49-7.75 (m, 4H), 7.94-7.98 (m, 3H), 9.11 (bs, 1H), 9.70 (bs, 1H).

Example 55

Free Base $^1$H-NMR (400 MHz, DMSO-d$_6$): δ 1.56-1.69 (m, 1H), 2.32-2.34 (m, 1H), 2.76-2.90 (m, 3H), 3.23 (q, J=2.0 Hz, 1H), 3.4 (bs, 1H), 3.62 (t, J=2.3 Hz, 1H), 3.98 (dd, J=0.80, J=1.9 Hz, 1H), 7.30 (s, 1H), 7.45 (s, 1H), 7.59-7.70 (m, 3H), 7.95 (d, J=1.9 Hz, 1H).

Example 56

Free Base $^1$H-NMR (400 MHz, DMSO-d$_6$): δ 1.56-1.67 (m, 1H), 2.27-2.39 (m, 1H), 2.73-2.91 (m, 3H), 3.23 (q, J=2.0 Hz, 1H), 3.4 (bs, 1H), 3.62 (t, J=2.2 Hz, 1H), 3.98 (d, J=2.8 Hz, 1H), 7.29 (s, 1H), 7.45 (s, 1H), 7.59-7.70 (m, 3H), 7.95 (d, J=1.9 Hz, 1H).

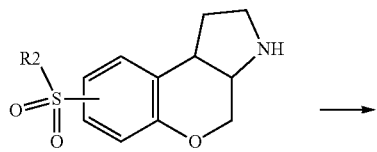

i. R3R4C═O, DCM:MeOH (9:1), DIEA, NaCNBH3, THF, AcOH. ii. R3R4-Br, DIEA, DMF.

Example 57

7-(Phenylsulfonyl)-3-(propan-2-yl)-1,2,3,3a,4,9b-hexahydrochromeno[3,4-b]pyrrole 7-(Phenylsulfonyl)-1,2,3,3a,4,9b-hexahydrochromeno[3,4-b]pyrrole hydrochloride (enantiomer 1, Example 55, 20 mg, 0.08 mmol) was dissolved in 500 μL DCE:MeOH (9:1). After 10 min stirring, propan-2-one (7 μL, 1.5 eq), a 1 M solution of sodium cyanoborohydride in THF (0.16 mL, 0.16 mmol) and acetic acid (50 μL) were added sequentially. After stirring for 16 h, the reaction mixture was passed through a plug of silica gel and the solvent was evaporated. The residue was purified by preparative LC/MS using the standard procedure. The resulting material was dissolved in a small amount of DCM, treated with 1.0 N HCl in diethyl ether and the solvent evaporated to provide 7-(phenylsulfonyl)-3-(propan-2-yl)-1,2,3,3a,4,9b-hexahydrochromeno[3,4-b]pyrrole hydrochloride. MS m/z 358.1 [M+H]$^+$. $^1$H-NMR (400 MHz, DMSO-d$_6$): δ 1.30 (d, J=1.6 Hz, 3H), 1.35 (d, J=1.6 Hz, 3H), 1.83-1.88 (m, 1H), 2.62-2.66 (m, 1H), 3.21-3.24 (m, 1H), 3.37 (bs, 1H), 3.66-3.72 (m, 2H), 4.10-4.24 (m, 3H), 4.23-4.41 (m, 1H), 7.45 (s, 1H), 7.52-7.77 (m, 5H), 7.97 (d, J=2 Hz 1H), 10.4 (bs, 1H).

The following examples were prepared essentially as described above. All of the following compounds were isolated as HCl salts.

| Ex. No. | Chemical Name | MS m/z, [M + H]$^+$ | Stereochemistry | Scaffold | Starting material |
|---|---|---|---|---|---|
| 57 | 7-(phenylsulfonyl)-3-(propan-2-yl)-1,2,3,3a,4,9b-hexahydrochromeno[3,4-b]pyrrole | 358.1 | Enantiomer 1 | Example 55 | propan-2-one |
| 58 | 7-(phenylsulfonyl)-3-(propan-2-yl)-1,2,3,3a,4,9b-hexahydrochromeno[3,4-b]pyrrole | 358.1 | Enantiomer 2 | Example 56 | propan-2-one |
| 59 | 3-cyclobutyl-7-(phenylsulfonyl)-1,2,3,3a,4,9b-hexahydrochromeno[3,4-b]pyrrole | 370.1 | Enantiomer 1 | Example 55 | cyclobutanone |
| 60 | 3-cyclobutyl-7-(phenylsulfonyl)-1,2,3,3a,4,9b-hexahydrochromeno[3,4-b]pyrrole | 370.1 | Enantiomer 2 | Example 56 | cyclobutanone |
| 61 | 3-cyclopentyl-7-(phenylsulfonyl)-1,2,3,3a,4,9b-hexahydrochromeno[3,4-b]pyrrole | 384.2 | Enantiomer 1 | Example 55 | cyclopentanone |
| 62 | 3-cyclopentyl-7-(phenylsulfonyl)-1,2,3,3a,4,9b-hexahydrochromeno[3,4-b]pyrrole | 384.2 | Enantiomer 2 | Example 56 | cyclopentanone |
| 63 | 3-cyclohexyl-7-(phenylsulfonyl)-1,2,3,3a,4,9b-hexahydrochromeno[3,4-b]pyrrole | 398.2 | Enantiomer 1 | Example 55 | cyclohexanone |
| 64 | 3-cyclohexyl-7-(phenylsulfonyl)-1,2,3,3a,4,9b- | 398.2 | Enantiomer 2 | Example 56 | cyclohexanone |

-continued

| Ex. No. | Chemical Name | MS m/z, [M + H]+ | Stereochemistry | Scaffold | Starting material |
|---|---|---|---|---|---|
| | hexahydrochromeno[3,4-b]pyrrole | | | | |
| 65 | 7-(phenylsulfonyl)-3-(tetrahydrofuran-3-yl)-1,2,3,3a,4,9b-hexahydrochromeno[3,4-b]pyrrole | 386.1 | Enantiomer 1 | Example 55 | dihydrofuran-3(2H)-one |
| 66 | 7-(phenylsulfonyl)-3-(tetrahydrofuran-3-yl)-1,2,3,3a,4,9b-hexahydrochromeno[3,4-b]pyrrole | 386.1 | Enantiomer 2 | Example 56 | dihydrofuran-3(2H)-one |
| 67 | 3-(2,2-difluoroethyl)-7-(phenylsulfonyl)-1,2,3,3a,4,9b-hexahydrochromeno[3,4-b]pyrrole | 380.1 | Enantiomer 1 | Example 55 | 1-ethoxy-2,2-difluoroethanol |
| 68 | 7-(phenylsulfonyl)-3-(tetrahydro-2H-pyran-4-yl)-1,2,3,3a,4,9b-hexahydrochromeno[3,4-b]pyrrole | 400.2 | Enantiomer 1 | Example 55 | tetrahydro-4H-pyran-4-one |
| 69 | 7-(phenylsulfonyl)-3-(tetrahydro-2H-pyran-4-yl)-1,2,3,3a,4,9b-hexahydrochromeno[3,4-b]pyrrole | 400.2 | Enantiomer 2 | Example 56 | tetrahydro-4H-pyran-4-one |
| 70 | 3-(cyclopentylmethyl)-7-(phenylsulfonyl)-1,2,3,3a,4,9b-hexahydrochromeno[3,4-b]pyrrole | 398.2 | Enantiomer 1 | Example 55 | cyclopentane carbaldehyde |
| 71 | 3-(cyclopentylmethyl)-7-(phenylsulfonyl)-1,2,3,3a,4,9b-hexahydrochromeno[3,4-b]pyrrole | 398.2 | Enantiomer 2 | Example 56 | cyclopentane carbaldehyde |
| 72 | 3-(cyclopropylmethyl)-7-(phenylsulfonyl)-1,2,3,3a,4,9b-hexahydrochromeno[3,4-b]pyrrole | 370.1 | Enantiomer 2 | Example 56 | cyclopropane carbaldehyde |
| 73 | 7-[(5-bromopyridin-3-yl)sulfonyl]-3-cyclobutyl-1,2,3,3a,4,9b-hexahydrochromeno[3,4-b]pyrrole | 449.0 | Enantiomer 1 | Example 28 | cyclobutanone |
| 74 | 3-cyclobutyl-7-[(5-methoxypyridin-3-yl)sulfonyl]-1,2,3,3a,4,9b-hexahydrochromeno[3,4-b]pyrrole | 401.1 | Enantiomer 1 | Example 33 | cyclobutanone |
| 75 | 3-cyclobutyl-7-[(5-fluoropyridin-3-yl)sulfonyl]-1,2,3,3a,4,9b-hexahydrochromeno[3,4-b]pyrrole | 389.1 | Enantiomer 1 | Example 29 | cyclobutanone |
| 76 | 7-[(5-chloropyridin-3-yl)sulfonyl]-3-cyclobutyl-1,2,3,3a,4,9b-hexahydrochromeno[3,4-b]pyrrole | 405.1 | Enantiomer 1 | Example 30 | cyclobutanone |
| 77 | 3-(2,2-difluoroethyl)-7-(phenylsulfonyl)-1,2,3,3a,4,9b-hexahydrochromeno[3,4-b]pyrrole | 380.1 | Enantiomer 2 | Example 56 | 1-ethoxy-2,2-difluoroethanol |
| 78 | 7-[(5-bromopyridin-3-yl)sulfonyl]-3-cyclobutyl-1,2,3,3a,4,9b-hexahydrochromeno[3,4-b]pyrrole | 449.0 | Enantiomer 2 | Example 31 | cyclobutanone |
| 79 | 3-cyclobutyl-7-[(5-methoxypyridin-3-yl)sulfonyl]-1,2,3,3a,4,9b-hexahydrochromeno[3,4-b]pyrrole | 401.1 | Enantiomer 2 | Example 35 | cyclobutanone |
| 80 | 3-cyclobutyl-7-[(5-fluoropyridin-3-yl)sulfonyl]-1,2,3,3a,4,9b-hexahydrochromeno[3,4-b]pyrrole | 389.1 | Enantiomer 2 | Example 32 | cyclobutanone |

-continued

| Ex. No. | Chemical Name | MS m/z, [M + H]+ | Stereochemistry | Scaffold | Starting material |
|---|---|---|---|---|---|
| 81 | 7-[(5-chloropyridin-3-yl)sulfonyl]-3-cyclobutyl-1,2,3,3a,4,9b-hexahydrochromeno[3,4-b]pyrrole | 405.1 | Enantiomer 2 | Example 34 | cyclobutanone |
| 82 | 3-cyclobutyl-7-[(6-methylpyridin-2-yl)sulfanyl]-1,2,3,3a,4,9b-hexahydrochromeno[3,4-b]pyrrole | 353.2 | Enantiomer 1 | Example 21 | cyclobutanone |
| 83 | 3-cyclobutyl-7-[(6-methylpyridin-2-yl)sulfinyl]-1,2,3,3a,4,9b-hexahydrochromeno[3,4-b]pyrrole | 369.2 | Enantiomer 1 | Example 22 | cyclobutanone |
| 84 | 3-cyclobutyl-7-[(6-methylpyridin-2-yl)sulfonyl]-1,2,3,3a,4,9b-hexahydrochromeno[3,4-b]pyrrole | 385.2 | Enantiomer 1 | Example 23 | cyclobutanone |
| 85 | 3-cyclobutyl-7-[(6-methylpyridin-2-yl)sulfonyl]-1,2,3,3a,4,9b-hexahydrochromeno[3,4-b]pyrrole | 385.2 | Enantiomer 2 | Example 24 | cyclobutanone |
| 86 | 3-cyclobutyl-7-{[5-(trifluoromethyl)pyridin-3-yl]sulfonyl}-1,2,3,3a,4,9b-hexahydrochromeno[3,4-b]pyrrole | 439.1 | Enantiomer 1 | Example 51 | cyclobutanone |
| 87 | 3-cyclobutyl-7-{[5-(trifluoromethyl)pyridin-3-yl]sulfonyl}-1,2,3,3a,4,9b-hexahydrochromeno[3,4-b]pyrrole | 439.1 | Enantiomer 2 | Example 52 | cyclobutanone |
| 88 | 3-cyclobutyl-8-(phenylsulfonyl)-1,2,3,3a,4,9b-hexahydrochromeno[3,4-b]pyrrole | 370.1 | Enantiomer 1 | Example 53 | cyclobutanone |
| 89 | 3-cyclobutyl-8-(phenylsulfonyl)-1,2,3,3a,4,9b-hexahydrochromeno[3,4-b]pyrrole | 370.1 | Enantiomer 2 | Example 54 | cyclobutanone |

Example 88

$^1$H-NMR (400 MHz, DMSO-$d_6$): δ 1.67-1.91 (m, 3H), 2.13-2.20 (m, 1H), 2.26-2.36 (m, 3H), 2.69-2.78 (m, 1H), 3.06-3.14 (m, 1H), 3.32-3.39 (m, 1H), 3.85 (q, J=1.8 Hz 1H), 3.93-4.11 (m, 2H), 4.28-4.36 (m, 2H), 7.11 (d, J=2.1 Hz, 1H), 7.56-7.76 (m, 4H), 7.98-8.01 (m, 3H), 10.6 (s, 1H).

Example 89

$^1$H-NMR (400 MHz, DMSO-$d_6$): δ 1.67-1.89 (m, 3H), 2.13-2.20 (m, 1H), 2.26-2.37 (m, 3H), 2.71-2.76 (m, 1H), 3.08-3.12 (m, 1H), 3.32-3.37 (m, 1H), 3.85 (q, J=1.8 Hz 1H), 3.91-4.01 (m, 2H), 4.28-4.36 (m, 2H), 7.11 (d, J=2.2 Hz, 1H), 7.59-7.75 (m, 4H), 7.94-7.98 (m, 3H), 10.6 (s, 1H).

Example 90

2-[7-(Phenylsulfonyl)-1,3a,4,9b-tetrahydrochromeno[3,4-b]pyrrol-3(2H)-yl]ethanol

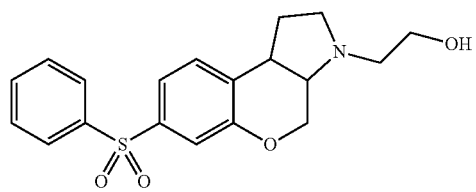 [SMILES: O=S(=O)(c1ccccc1)c1ccc2c(c1)OCC1C2CCN1CCO]

A 0.20 N stock solution of 7-(phenylsulfonyl)-1,2,3,3a,4,9b-hexahydrochromeno[3,4-b]pyrrole hydrochloride (enantiomer 1, Example 55, 343 mg, 0.8 mmol) in DMF (4 mL) was prepared. To 400 µL (0.08 mmol) of this stock solution was added DIEA (21 µL, 1.5 eq) and 1-bromoethanol (9 µL, 0.9 eq). The reaction was stirred at 60° C. for 16 h and the solvent was evaporated. The resulting crude product was purified by preparative LC/MS and concentrated to afford the product as a trifluoroacetic acid salt. Conversion to the HCl salt was accomplished by dissolving the product in DCM, adding 1M HCl in Et$_2$O and evaporating the solvent. MS m/z 360.1 [M+H]+. $^1$H-NMR (400 MHz, DMSO-$d_6$): δ 1.71 (bs, 1H), 2.69 (bs, 1H), 3.25 (bs, 2H), 3.55 (bs, 2H), 3.70-3.83 (m, 3H), 4.12 (bs, 1H), 4.23-4.32 (m, 2H), 5.36 (bs, 1H), 7.43 (bs, 1H), 7.52-7.68 (m, 6H), 7.97 (d, J=2 Hz 1H), 10.0 (bs, 1H).

The following examples were prepared essentially as described in the above synthetic steps. All compounds were isolated as HCl salts.

| Ex No. | Chemical Name | MS m/z, [M + H]+ | Stereochemistry | Scaffold | Starting material |
|---|---|---|---|---|---|
| 90 | 2[7-(phenylsulfonyl)-1,3a,4,9b-tetrahydrochromeno[3,4-b]pyrrol-3(2H)-yl]ethanol | 360.1 | Enantiomer 1 | Example 55 | 2-bromoethanol |
| 91 | 3-(2-methylpropyl)-7-(phenylsulfonyl)-1,2,3,3a,4,9b-hexahydrochromeno[3,4-b]pyrrole | 372.2 | Enantiomer 1 | Example 55 | 1-bromo-2-methylpropane |
| 92 | 3-(2-methoxyethyl)-7-(phenylsulfonyl)-1,2,3,3a,4,9b-hexahydrochromeno[3,4-b]pyrrole | 374.1 | Enantiomer 1 | Example 55 | 1-bromo-2-methoxyethane |
| 93 | 3[7-(phenylsulfonyl)-1,3a,4,9b-tetrahydrochromeno[3,4-b]pyrrol-3(2H)-yl]propan-1-ol | 374.1 | Enantiomer 1 | Example 55 | 3-bromopropan-1-ol |
| 94 | 3-(4-methylpentyl)-7-(phenylsulfonyl)-1,2,3,3a,4,9b-hexahydrochromeno[3,4-b]pyrrole | 400.2 | Enantiomer 1 | Example 55 | 1-bromo-4-methylpentane |
| 95 | 3-benzyl-7-(phenylsulfonyl)-1,2,3,3a,4,9b-hexahydrochromeno[3,4-b]pyrrole | 406.1 | Enantiomer 1 | Example 55 | (bromomethyl)benzene |
| 96 | 3-(2-phenylethyl)-7-(phenylsulfonyl)-1,2,3,3a,4,9b-hexahydrochromeno[3,4-b]pyrrole | 420.2 | Enantiomer 1 | Example 55 | (2-bromoethyl)benzene |
| 97 | 2-[7-(phenylsulfonyl)-1,3a,4,9b-tetrahydrochromeno[3,4-b]pyrrol-3(2H)-yl]ethanol | 360.1 | Enantiomer 2 | Example 56 | 2-bromoethanol |
| 98 | 3-(2-methylpropyl)-7-(phenylsulfonyl)-1,2,3,3a,4,9b-hexahydrochromeno[3,4-b]pyrrole | 372.2 | Enantiomer 2 | Example 56 | 1-bromo-2-methylpropane |
| 99 | 3-(2-methoxyethyl)-7-(phenylsulfonyl)-1,2,3,3a,4,9b-hexahydrochromeno[3,4-b]pyrrole | 374.1 | Enantiomer 2 | Example 56 | 1-bromo-2-methoxyethane |
| 100 | 3-[7-(phenylsulfonyl)-1,3a,4,9b-tetrahydrochromeno[3,4-b]pyrrol-3(2H)-yl]propan-1-ol | 374.1 | Enantiomer 2 | Example 56 | 3-bromopropan-1-ol |
| 101 | 3-(4-methylpentyl)-7-(phenylsulfonyl)-1,2,3,3a,4,9b-hexahydrochromeno[3,4-b]pyrrole | 400.2 | Enantiomer 2 | Example 56 | 1-bromo-4-methylpentane |
| 102 | 3-benzyl-7-(phenylsulfonyl)-1,2,3,3a,4,9b-hexahydrochromeno[3,4-b]pyrrole | 406.1 | Enantiomer 2 | Example 56 | (bromomethyl)benzene |
| 103 | 3-(2-phenylethyl)-7-(phenylsulfonyl)-1,2,3,3a,4,9b-hexahydrochromeno[3,4-b]pyrrole | 420.2 | Enantiomer 2 | Example 56 | (2-bromoethyl)benzene |

Examples 104, 105, 106, 107, 108, 109, 110, 111 in the table below were prepared essentially as described for example 1 starting from racemic tert-butyl 7-iodo-1,3a,4,9b-tetrahydrochromeno[3,4-b]pyrrole-3(2H)-carboxylate P01 and the corresponding thiol. All of the following compounds were isolated as HCl salts.

| Entry | Chemical Name | MS m/z, [M + H]+ | Stereochemistry | Starting material |
|---|---|---|---|---|
| Example 104 | 7-(phenylsulfonyl)-1,2,3,3a,4,9b-hexahydrochromeno[3,4-b]pyrrole | 316.1 | racemic | benzenethiol |
| Example 105 | 7-[(3,5-difluorophenyl)sulfonyl]- | 352.1 | racemic | 3,5-difluorobenzenethiol |

-continued

| Entry | Chemical Name | MS m/z, [M + H]+ | Stereochemistry | Starting material |
|---|---|---|---|---|
| Example 106 | 1,2,3,3a,4,9b-hexahydrochromeno[3,4-b]pyrrole 7-(phenylsulfinyl)-1,2,3,3a,4,9b-hexahydrochromeno[3,4-b]pyrrole | 300.1 | racemic | benzenethiol |
| Example 107 | 7-{[3-(propan-2-yloxy)phenyl]sulfonyl}-1,2,3,3a,4,9b-hexahydrochromeno[3,4-b]pyrrole | 374.1 | racemic | 3-(propan-2-yloxy)benzenethiol |
| Example 108 | 7-{[3-fluoro-5-(propan-2-yloxy)phenyl]sulfonyl}-1,2,3,3a,4,9b-hexahydrochromeno[3,4-b]pyrrole | 392.1 | racemic | 1-fluoro-3-iodo-5-(propan-2-yloxy)benzene |
| Example 109 | 7-[(3-fluoro-5-methoxyphenyl)sulfonyl]-1,2,3,3a,4,9b-hexahydrochromeno[3,4-b]pyrrole | 364.1 | racemic | 1-fluoro-3-iodo-5-methoxybenzene |
| Example 110 | 7-[(5-methoxypyridin-3-yl)sulfonyl]-1,2,3,3a,4,9b-hexahydrochromeno[3,4-b]pyrrole | 347.1 | racemic | 3-iodo-5-methoxypyridine |
| Example 111 | 7-[(5-chloropyridin-3-yl)sulfonyl]-1,2,3,3a,4,9b-hexahydrochromeno[3,4-b]pyrrole | 351.0 | racemic | 3-chloro-5-iodopyridine |

SM01

1-Ethoxy-3-fluoro-5-iodobenzene

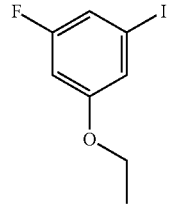

(3-Ethoxy-5-fluorophenyl)boronic acid (2.5 g, 0.014 mol) was dissolved in THF (30 mL) and a solution of sodium iodide (4.1 g, 0.028 mol) in H₂O (15 mL) was added followed by a solution of chloramine T (7.8 g, 0.1 mol) in H₂O (15 mL). After 20 h stirring, the reaction mixture was extracted with diethylether (3×50 mL). The organic layers were combined and the solvent was evaporated. The resulting residue was triturated with hexanes (3×) and the hexanes layers were combined. The solvent was evaporated to yield 1-Ethoxy-3-fluoro-5-iodobenzene as an orange oil. The product was used in the next reaction step without further purification.

The following examples were prepared essentially as described immediately above.

| Preparation | Chemical name | Starting material |
|---|---|---|
| SM01 | 1-ethoxy-3-fluoro-5-iodobenzene | (3-ethoxy-5-fluorophenyl)boronic acid |
| SM02 | 1-fluoro-3-iodo-5-methoxybenzene | (3-fluoro-5-methoxyphenyl)boronic acid |
| SM03 | 1-fluoro-3-iodo-5-(propan-2-yloxy)benzene | [3-fluoro-5-(propan-2-yloxy)phenyl]boronic acid |
| SM04 | 1-fluoro-3-iodo-5-(2-methylpropoxy)benzene | [3-fluoro-5-(2-methylpropoxy)phenyl]-boronic acid |

SM05

3-Iodo-N,N-dimethylbenzamide

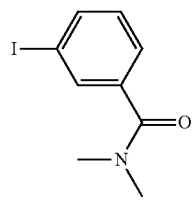

EDCl (1.3 g, 6.6 mmol) was added to a solution of dimethylamine in THF (2 M, 6 mL, 10 mmol) and 3-iodobenzoic acid (1.5 g, 6 mmol). After 18 h stirring the reaction was transferred into water, and then extracted with ethyl acetate. The organic phase was dried over sodium sulfate. The solvent was evaporated to afford the product as a viscous, clear oil.

The product was used in the next reaction step without further purification. MS m/z: 276 [M+H].

SM06

3-Trifluoromethyl-5-triisopropylsilanylsulfanyl-pyridine

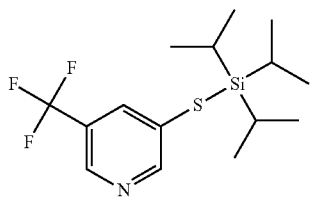 [SMILES: CC(C)[Si](Sc1cncc(C(F)(F)F)c1)(C(C)C)C(C)C]

Anhydrous toluene was sparged with argon gas for 1 h before being used. Palladium acetate (0.050 g, 0.22 mmol), triphenylphosphine (0.255 g, 0.973 mmol), cesium carbonate (1.87 g, 5.75 mmol) and 3-bromo-5-trifluoromethyl-pyridine (1.00 g, 4.42 mmol) were introduced into a 50 mL round bottom flask under argon. Toluene (10 mL) and triisopropyl-silanethiol (1.23 mL, 5.75 mmol) were added. The reaction was stirred at 100° C. overnight, then cooled to room temperature and diluted with hexanes. The suspension was filtered through a plug of Celite. The filtrate was concentrated to afford 3-trifluoromethyl-5-triisopropylsilanylsulfanyl-pyridine which was used in the next reaction step without further purification.

The invention claimed is:

1. A compound of Formula I

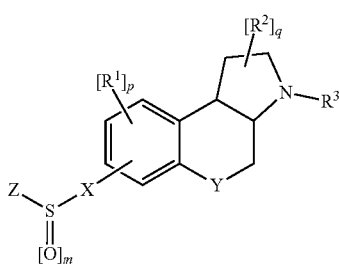

or a salt thereof, wherein:
R$^1$ at each occurrence is independently selected from H, halogen, NR$^5$R$^6$, (C$_1$-C$_6$)alkyl, and (C$_1$-C$_6$)alkoxy, and p is 0, 1, or 2;
R$^2$ at each occurrence is independently selected from H and (C$_1$-C$_6$)alkyl, and q is 0, 1, or 2;
R$^3$ is selected from H, (C$_1$-C$_6$)alkyl, (C$_1$-C$_6$)hydroxyalkyl, (C$_1$-C$_6$)haloalkyl, (C$_1$-C$_6$)alkyl(C$_1$-C$_6$)alkoxy, CO(C$_1$-C$_6$)alkyl, CO$_2$(C$_1$-C$_6$)alkyl, (C$_1$-C$_6$)alkyl(C$_6$-C$_{10}$)aryl, (C$_3$-C$_6$)cycloalkyl, (C$_1$-C$_6$)alkyl(C$_3$-C$_6$)cycloalkyl, (C$_2$-C$_9$)heterocycloalkyl, (C$_1$-C$_6$)alkyl(C$_2$-C$_9$)heterocycloalkyl;
Y is CH$_2$ or O;
X is absent;
R$^5$ and R$^6$ are H;
m is 1 or 2; and
Z is selected from (C$_6$-C$_{10}$)aryl, and (C$_2$-C$_9$)heteroaryl, wherein any of the foregoing is optionally substituted with one, two or three substituents selected from halogen, (C$_1$-C$_6$)alkyl, (C$_1$-C$_6$)haloalkyl, (C$_1$-C$_6$)alkoxy, O(C$_1$-C$_6$)haloalkyl, CONH(C$_1$-C$_6$)alkyl, and CON((C$_1$-C$_6$)alkyl)$_2$; wherein,
when Z is (C$_6$-C$_{10}$)aryl, Z is selected from phenyl and naphthyl, and
when Z is (C$_5$-C$_9$)heteroaryl, Z is selected from pyridyl and:

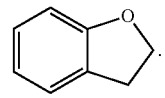

2. A compound according to claim 1 having the structure of Formula II

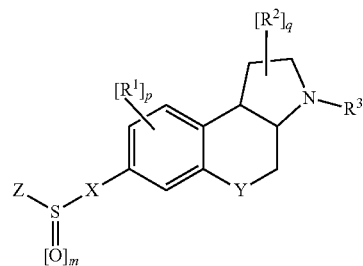

or a salt thereof.

3. A compound according to claim 2 or a salt thereof, wherein: p and q are each 0.

4. A compound according to claim 1 having the structure of Formula III

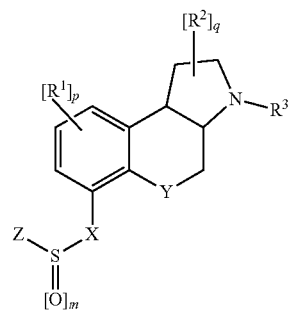

or a salt thereof.

5. A compound according to claim 1 having the structure of Formula IV

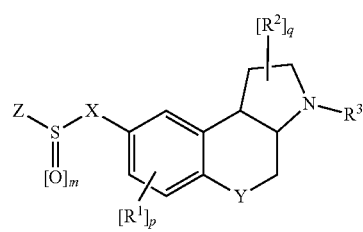

or a salt thereof.

6. A compound according to claim 1 having the structure of Formula V
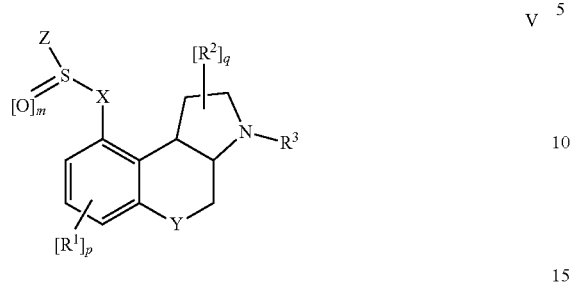
V
or a salt thereof.
7. A composition comprising a compound according to claim 1, or a pharmaceutically acceptable salt thereof, and at least one pharmaceutically acceptable excipient.
* * * * *